United States Patent
Forster et al.

(10) Patent No.: US 7,317,136 B1
(45) Date of Patent: Jan. 8, 2008

(54) METHODS FOR MODIFYING PLANT CELL WALLS AND MODIFIED PLANTS PRODUCED THEREBY

(75) Inventors: Richard L. Forster, Auckland (NZ);
Jeroen Demmer, Auckland (NZ);
Murray R. Grigor, Auckland (NZ);
Sathish Puthigae, Auckland (NZ);
Jonathan Phillips, Auckland (NZ)

(73) Assignee: Arborgen, LLC, Summerville, SC (US)

( * ) Notice: Subject to any disclaimer, the term of this patent is extended or adjusted under 35 U.S.C. 154(b) by 309 days.

(21) Appl. No.: 10/198,232

(22) Filed: Jul. 17, 2002

Related U.S. Application Data

(60) Provisional application No. 60/306,267, filed on Jul. 17, 2001, provisional application No. 60/306,327, filed on Jul. 17, 2001, provisional application No. 60/345,397, filed on Nov. 9, 2001.

(51) Int. Cl.
*C12N 15/82* (2006.01)
(52) U.S. Cl. .................. 800/278; 800/287; 800/290
(58) Field of Classification Search ................ 800/278, 800/298, 287, 285, 290; 435/468, 419
See application file for complete search history.

(56) References Cited

FOREIGN PATENT DOCUMENTS

WO     WO 00/71670     11/2000

OTHER PUBLICATIONS

Yang et al (2001, PNAS 98(20):11438-11443).*
Riechmann et al (2000, Current Opinion in Plant Biology 3:423-434).*
Kawaoka et al (2000, The Plant Journal 22(4):289-301).*
Richmond, Todd, "Higher plant cellulose synthases," *GTenome Biology 2000*, Vol. 1., No. 4, reviews 3001.1-3001.6 (Oct. 13, 2000).

* cited by examiner

*Primary Examiner*—Stuart F. Baum
(74) *Attorney, Agent, or Firm*—Foley and Lardner LLP

(57) ABSTRACT

The present invention provides methods for modulating cellulose, hemicellulose and lignin composition and deposition in secondary cell wall layers of plants to improve plant traits that are commercially desirable (e.g., enhanced digestibility of forage crops by animals, increased post-harvest processing of wood and crops for energy production and pulping, increase mechanical strength of plants, and others). The invention also provides methods for identifying genes encoding transcription factors that regulate the formation of secondary cell walls, polynucleotide sequences that encode key components of secondary cell walls, and transgenic plants comprising these sequences.

3 Claims, 1 Drawing Sheet

MEVDANSGKSSKQIGSGQVCQICSDSVGTTADGEPFVACDVCAFPVCRPCYEYERKDGNQ    60

SCPQCKTKYKWHKGSPPVNGEAVEDGDGNGVTGAQERHHKLPERTLSWDTNYDKEGSFNH    120

IPLLTTGRSVSGELSA    136

FIG. 1

SEQUENCE LISTING

```
<160> NUMBER OF SEQ ID NOS: 96

<210> SEQ ID NO 1
<211> LENGTH: 555
<212> TYPE: DNA
<213> ORGANISM: Cucurbita maxima

<400> SEQUENCE: 1
gctcaccatt ttcgaccaat ccccatttca ctttgctctc tcacaactca agatctctag       60
tttccatgaa gtgaaccaga gttgttcctt tcacttctgc ttgtttcact taaaatcgag      120
caggatcttc gagtggacca gcttccatgg aggtcgacgc taattcaggg aaatcgtcga      180
aacagattgg gagtggtcag gtttgtcaga tctgcagcga ttccgtcggc accacggccg      240
atggcgagcc gtttgttgcg tgtgatgttt gtgcatttcc ggtttgccgt ccttgttacg      300
```

```
agtacgagag gaaagatggg aatcagtctt gccctcagtg caaaaccaaa tacaagtggc    360
ataaaggaag tcctccggtt aatggagaag cagtggaaga tggggatggt aatggagtga    420
cgggggctca agaaaggcac cataagttac ctgagcgcac tcttagctgg gataccaact    480
atgataagga gggatccttt aatcatattc ctttgcttac cactggacga tctgtttctg    540
gagaactatc agctg                                                    555
```

```
<210> SEQ ID NO 2
<211> LENGTH: 674
<212> TYPE: DNA
<213> ORGANISM: Cucurbita maxima

<400> SEQUENCE: 2
ggatggttca gcaatgctta cgtttgaatc gctctctgaa actgcagagt ttgcaaggaa     60
gtgggtgcct ttttgcaaga agcatagcat tgaaccaagg gccccagagt tttatttttgc   120 tcaaaagata gattacttga aggacaagat taaaccttcg ttcgtaaaag agcgtcgagc    180
gatgaagagg gaatatgaag aattcaagat tcgaatcaat gcacttgttg ccaaagcaca    240
aaagatgcct gaggaaggtt ggaccatgca ggatggaacg ccatggccag gaaacaatcc    300
cagggatcat cctggaatga tacaggtttt cttaggccac agtggaggtc tcgataccga    360 tgcaatgaa ctacctagac ttgttttatgt ttctcgtgag aaacgtcccg gcttccagca    420
ccacaaaaaa gctggagcta tgaatgcatt gatccgagtt tctgccgtgc taactaacgg    480
agcgtatcta ttgaatgtcg attgtgatca ctactttaac aacagcaaag ctctgaagga    540
agccatgtgt ttcatgatgg accctgctta tgggaagaaa acatgttacg tacagttccc    600
acaacgtttt gatggcattg atttgcacga tcgatatgcc aatcgtaaca ttgtcttttt    660
cgacataaac ttga                                                     674
```

```
<210> SEQ ID NO 3
<211> LENGTH: 1350
<212> TYPE: DNA
<213> ORGANISM: Cucurbita maxima

<400> SEQUENCE: 3
gggagaaact taccttgatc ggttatcgtt aagatatgaa aaagatggca agccatctga     60
gttggcttct atagacattt atgtcagtac tgtggatcca ttgaaggagc ctcctctcat    120
cacggcaaac accgtcctgt ctattcttgc cgtcgattat ccagtagaca aggtttcatg    180
ctacgtttcg gacgatggtg ctgccatgct tacttttgaa gcccttttccg aaacttctga   240 gtttgcaaga agtgggttc ctttctgcaa gaagttcaat atcgaacctc gggccccaga    300
atggtatttt gccctgaagg tcgattattt gaaagataaa gttgatccaa ccttcatccg    360
ggaaagacgt gcaatgaaga gggactatga agaatttaaa gttcgaatca atgggctcgt    420
tgccatggct caaaaagttc ctgaagacgg gtggacaatg caggacgaa ctccatggcc     480 cgggaacaac gtcagggatc atcctggaat gattcaggta ttcctcggtt caacgggggt    540
tcgtgatttg gagggaaatg aattacctcg tttagtgtat gtatctcgtg agaagaggcc    600
gggattcgat caccacaaga agctggtgc catgaatgct ctggtgcgtg tatcggcaat    660
catttcaaac gctccatacg cacgaggccg tggactaccc agtggacaaa gtttcgtgct    720
atgtatcaga cgatggttca gcaatgctta catttgaagc gctctctgaa actgcagagt    780
ttgcaaggaa gtgggttccc ttttgcaaga agcacaacat tgagccaagg gcccctgaat    840 tttatttttgc tcaaaaaata gactacttga aggacaagat taagccttct tttgttaaag    900
```

```
agcggcgggc aatgaagaga gagtacgaag aattcaaggt tcgaatcaat gcacttgttg    960
ccaaagcaca aaagatgcct gaggaaggat ggaccatgca ggatggaacg gcatggcctg   1020
gaaacaatcc cagggatcat cctggaatga tacaggtttt cttaggtcac agtggaggtc   1080
ttgatactga tggaaatgaa ctgccacgac ttgtttatgt ttctcgtgag aagcgaccgg   1140
gtttccagca ccacaagaaa gccggagcta tgaatgcatt gatccgagtt tctgccgtgc   1200
ttacaaatgg agcatatctt ttgaatgtcg attgtgatca ctacttcaac aacagcaaag   1260
ctctcaagga agccatgtgt tcatgatgg accctgcata tgggaagaaa acatgttatg   1320
tacaattccc acaacgtttt gatggcattg                                    1350
```

<210> SEQ ID NO 4
<211> LENGTH: 634
<212> TYPE: DNA
<213> ORGANISM: Cucumis sativa

<400> SEQUENCE: 4

```
gcttttcagt cggcattgtc ctgtatggta cggttatggt ggacggttga aatggcttga     60
gagatttgct tatgttaaca ccaccattta tccaataaca tccattcctc ttcttgccta    120
ttgtacctta cctgccatat gtttactcac gggaaagttt atcattcctc agatcagcaa    180
tcttgctagc atctggttca tctctctctt tctttccatc tttgctaccg gtattctgga    240
aatgagatgg agtggtgttg gaatcgatga atggtggaga aacgaacaat tctgggttat    300
tggaggtgtg tcgccccatc ttttcgctgt cttccaaggt cttcttaaag ttcttgctgg    360
aatcgataca aacttcacgg ttacttcgaa agcgtccgac gaagatggag attttgctga    420
gctctacatg ttcaagtgga ccactcttct gattccccca actactctcc taatcatcaa    480
catagttgga gttgttgctg gaatttctta tgcgatcaac agtggttatc aatcttgggg    540
accccttttc gggaaactgt tcttcgcttt ctgggtgatt attcatctgt atcccttcct    600
taagggtctg atgggtcgcc agaaccgaac accc                                634
```

<210> SEQ ID NO 5
<211> LENGTH: 600
<212> TYPE: DNA
<213> ORGANISM: Cucumis sativa

<400> SEQUENCE: 5

```
gcgtggttgg agatcgatct attgcatacc ggagcgtcct gcatttaaag ggtctgctcc     60
cattaatctt tctgatcgtc ttaaccaagt gcttcggtgg gcgttaggtt cggttgaaat    120
tctcttcagt cggcattgtc ctatgtggta cggttatggt ggacggttga aatggctcga    180
gcgatttgct tatgttaaca ctaccattta cccaataaca tcgattcctc ttcttgccta    240
ttgtacctta cctgcaatat gtctgctcac tggaaagttc atcattcctc agatcagtaa    300
tcttgccagc atctggttca tttcgctctt tctttccatc tttgctactg gtattctgga    360
aatgagatgg agcggtgtcg ggatcgatga atggtggaga aacgagcagt tctgggttat    420
cggaggtgtg tcggcccatc tgtttgctgt gttccaaggt cttcttaaag ttcttgctgg    480
gattgatacc aacttcacgg ttacttcaaa agcatctgat gaagatggag attttgctga    540
gctctacttg ttcaagtgga caactcttct cattccccca actactctcc ttattatcaa    600
```

<210> SEQ ID NO 6
<211> LENGTH: 678
<212> TYPE: DNA

<213> ORGANISM: Cucurbita maxima

<400> SEQUENCE: 6

```
gccaaggtcc ggtttatgtg ggaacgggat gtgtcttcaa tcgaactgca ttgtacggct      60
atgaacccccc cctcaagcct aagcataaaa acccggggt cttctccagt tgctttggga     120
aatcaaaaaa gaaagttct aaatctaaaa ggaaggattc tgataaaaag caatcaaata      180
aaaacgtcga tcccactgtg ccgatattca acctcgagga tatcgaggaa ggtgttgaag     240
gtgctggatt tgacgatgag aagtcgctac taatgtcaca aatgagcctg agaagaggt      300
ttggtcaatc agctgtattt gttgcttcca cactgatgga gaatggtggc gtgccgcagt    360
ctgccacccc ggaatctctt cttaaggaag caattcacgt catcagttgc ggatacgagg    420
ataaaacaga ctggggaagt gaaattggat ggatctatgg ttctgtcaca gaagatattt    480
tgacagggtt caaaatgcac gcccgtggtt ggagatcgat ctattgcata cctgaccgtc   540
ctgcatttaa aggttctgcg cctattaatc tttccgatcg tctaaaccaa gtgcttcgat    600
gggcgctagg ttcagtcgaa attcttttca gtcggcattg cccgatgtgg tacggttata   660
gtggacgcct gaaatggc                                                   678
```

<210> SEQ ID NO 7
<211> LENGTH: 735
<212> TYPE: DNA
<213> ORGANISM: Cucurbita maxima

<400> SEQUENCE: 7

```
gttcaggtat tccttggtca aaacggtgtt cgtgacttgg agggaaatga attacctcgt     60
ctagtgtatg tatctcgtga gaagaggcca ggatttgatc accacaagaa agccggtgcc   120
atgaatgctt tggtgcgtgt ctcggcaatt atctcaaatg ctccatacat tttgaacgtc   180
gattgtgatc actacatcaa caacagcaag gctcttagag aagcaatgtg cttcatgatg   240
gacccaattt caggaaaaag aatatgctat gtgcagtttc cacaaagatt tgatgggatt   300
gataggcacg atcgatactc aaatcgaaat gttgtattct ttgatattaa catgaaagga   360
ttggacggta ttcaagggcc aatatacgtt ggaactggat gtgtctttag gaggcaagct   420
ctttatgggt atgatgcccc tgctaagaag aaagcaccaa gaaggacatg caactgtctt   480
ccaaaatggt gctgctgttg ctgtggaact agaaagaaga ctaaaacaaa gaccagtgat   540
aaaaagaaat taaagaccaa agatacgtcc aaacagattc acgcacttga aaatattgaa   600
gaaggaatcg aaggaataga taatgaaaaa tcatctctga tgccccaagt taagtttgag   660
aagaagtttg ggcaatcacc agcattcatt gcttccacac tcatggaaga tggtggcgtg   720
ccaggaggag ggact                                                     735
```

<210> SEQ ID NO 8
<211> LENGTH: 532
<212> TYPE: DNA
<213> ORGANISM: Cucumis sativa

<400> SEQUENCE: 8

```
ggtcgtgatc gatgattctt tactaaatga cgaagctcgc cagcctctat cgaggaaggt     60
ttctattcca tcctctagga ttaatcctta taggatggtc atcgttctcc ggcttattat    120
tctttgcatc ttcttgcact atcggattac aaatccagtt ccaaatgcct tgctctgtg    180
gttaatatca gtgatttgtg agatttggtt tgctatatct tggatttttgg atcagttccc  240
caaatggctc ccggttaatc gtgagacata tcttgatagg cttgctctga gatatgatcg   300
```

```
tgaaggagag ccatctcagt tggctgctgt cgacatattt gtcagtactg tcgaccctct    360
gaaagaacct cccttgtca ctgccaatac agtcctatca attctctctg tggactatcc     420
agttgataaa gtttcttgct acgtatctga tgatggagct gctatgttaa catttgaagc    480
tttgtccgaa acctcagaat tgctagaaa atgggttcct ttctgcaaga ag             532

<210> SEQ ID NO 9
<211> LENGTH: 554
<212> TYPE: DNA
<213> ORGANISM: Cucumis sativa

<400> SEQUENCE: 9 gcagggtat tctccagttg ctttgggaaa tcgaaaaaga aaagttctaa gtcaaaaga      60 aaggattctg acaagaagca atctagtaaa aatgttgatc ccacggtgcc aatattcaac    120
ctcgaagata ttgaggaagg agttgaaggt gctgggttg atgacgagaa atcactacta     180
atgtcgcaaa tgagcctgga gaagaggttt ggtcaatcag ctgtatttgt tgcttccaca   240
ctaatggaaa atggtggtgt gccgcaatct gccactccag aatctctcct taaagaagca    300
attcatgtca tcagttgtgg atacgaggat aaaacagact ggggaagtga aattggatgg    360
atctatggtt ccgtcacaga agatattttg acagggttca agatgcatgc ccgtggctgg    420
agatcaatct actgcatccc ggaccgtcct gcatttaaag gatctgctcc cattaatctt    480
tctgatcgtc ttaaccaagt gcttcggtgg gcgttaggtt cggttgaaat tcttttcagt    540
cggcattgtc ctgt                                                     554

<210> SEQ ID NO 10
<211> LENGTH: 404
<212> TYPE: DNA
<213> ORGANISM: Cucumis sativa

<400> SEQUENCE: 10
gggtggcgtg ccaggaggag ggacttctgc ttcattgttg aaagaagcca tacatgttat    60
cagttgtcgt tatgaagata atccgagtg gggtaaagag gttgggtgga tttatgggtc     120
tgttacagag gatattttaa caggtttcaa gatgcattgt catggatgga gatcagttta    180
ttgcattcct aaaagggcag cattcaaggg ttcagctcct attaacttgt ctgatcgtct    240
acaccaagtt cttcggtggg ctcttgggtc tgttgaaatt ctgttgagta ggcattgtcc    300
aatatggtac ggctatggat gtggtttgaa gtggcttgag cgtttctcat acataaactc    360
cgttgtgtat ccattgacgt cagttccact gattgcttat tgta                    404

<210> SEQ ID NO 11
<211> LENGTH: 703
<212> TYPE: DNA
<213> ORGANISM: Cucumis sativa
<220> FEATURE:
<221> NAME/KEY: misc_feature
<222> LOCATION: (1)...(703)
<223> OTHER INFORMATION: n = A,T,C or G

<400> SEQUENCE: 11
gtggctggtg ttaacacaaa tttcactgtc acatccaaag gaggagatga tgggattttt    60
gccgagcttt acctcttcaa atggacatca ttgttggtcc ctcccttgac cttattgatc    120
ataaacatta tcggagtagt tgtcggaatt tcagatgcca tcaacaatgg ttacgactca    180
tggggtccac tcattggtaa gctgttcttt gcattctggg tgattgtcca tctgtatcca    240
```

```
ttcctcaagg gtttgatggg gaagcaagac aaggtaccaa ctattatcat tgtgtggtca    300
atccttctat catccatttt gtcgctttta tgggtccgaa tcaacccctt cctcgacaag    360
ggtggcattg tgttggaagt ttgcgggtta aactgtgacg actaagatgc cgaaatacac    420
acgacatgaa ggattacggg taggagttgt gtttcaaatt tgtacgattg agcgtgggga    480
ctcactagtc ttgagcattt gttgaataga atacggtaac ggtactccac ccgagattgt    540
gaagcatgag tcagaagaaa gatgagttgc aaaaggctac ttgtcctgga ttgtagatat    600
ggaggaattt gcatatcaca catcatcaaa atatttgttc tctctgcaaa ctttgtcatt    660
gattcttttt tcttcttctt ctatacatgg gnttttttta ttt                     703

<210> SEQ ID NO 12
<211> LENGTH: 565
<212> TYPE: DNA
<213> ORGANISM: Cucumis sativa

<400> SEQUENCE: 12
ggggtgacgt caaaggccaa cgatgaagat ggagattttg cggagcttta tgtgttcaaa    60
tggacttctc tcctcatccc tcctaccact gtccttatta tgaatatggt tggtatagtg    120
gcaggtgttt catatgccat taacagtggt taccagtctt ggggtcctct ctttggcaag    180
ctgttctttg cattgtgggt tattgtccat ttatatcctt tcctaaaggg tttactagga    240
aggcaaaacc gtacacctac cattgtcatt gtctggtcca ttctcctcgc ttccattttc    300
tccttgctct gggtgcggat cgatccattc acctcggctg cgaccaaggc tgccaatggt    360
caatgtggtg tcaattgcta gacagttaca tcatagtttt gtcccgtggt atggcgtcgt    420
tcctgtgaat atgacaataa agaaatcaag gcattgagaa gagcccccag gaatgaacca    480
atttgaggaa aatgagaaaa ggatgacctt tacaccagaa tttgtaggtg tgtcttgaag    540
ttgtattggt atgttataat attat                                         565

<210> SEQ ID NO 13
<211> LENGTH: 584
<212> TYPE: DNA
<213> ORGANISM: Cucurbita maxima
<220> FEATURE:
<221> NAME/KEY: misc_feature
<222> LOCATION: (1)...(584)
<223> OTHER INFORMATION: n = A,T,C or G

<400> SEQUENCE: 13
ttcactttgc cctctcacgt ctccagaccc ctttttccat ctccaacttt gagtttccat    60
gaaagtaatc cagagttgtt cctttcactg ctgcttcttt tgcttaacac ccattacgat    120
cttcgactgg actagcagcc atggaggtcg atactaatcc tggngaaacc gctcgaaaca    180 gattggggc ggccaggttt gtcagatctg cagtgattcc gttggcacga cggccgacgg    240
cgagccgttt gttgcgtgtg atgtttgtgc atttccggtc tgccgtccat gttatgagta    300
cgagaggaaa gatgggaatc agtcttgccc tcaatgcaag actaaataca agtggcataa    360
aggaagtcct cctgttactg gtgaggcagt acaagatggt gatggcaatg gagtgggagg    420
ggcacaagaa aggcatcata agatgccaga gcgcaccctt agctgggata ctaattatga    480
taaagaggga tcttttaatc acattccttt gctcaccact ggacgatctg tttctggaga    540
actgtcagct gcatctcctg agcggctgtc catggcctct cctg                    584

<210> SEQ ID NO 14
<211> LENGTH: 590
```

```
<212> TYPE: DNA
<213> ORGANISM: Cucumis sativa

<400> SEQUENCE: 14
ggtatttgtg gcatgtttgg tgtgtaattt ccctgtttgt cgtccttgtt atgagtacga      60
aaggagcgaa ggcaacaagt gttgtcctca atgcaacact cgctacaagc gtcataaagg     120
ctcgcctaga gtcattggtg acgacgaaga agctgacgat gcagacgatt tcgacgatga     180
attccccatc aaacaccaca gtaatgatga gttcgaatca aaacagccca atccttcgga     240
acacgataac tacaaccaga agaattggca tcaaaacgtc catagttcct tctcagttgc     300
aggcagtgtg aatgggaagg agatggaggg cgagaaggaa agttatggaa atgctgaatg     360
gaaggagaga atagataagt ggaaagtgag gcaagaaag agaggtttgg ggaacaaaga      420
tgatgaaagt aaccatgatc aacccctaga agatgacttc ttattggcag aagcccggca     480
accactatgg cggaaggttc caatatcgtc gagcaaaatc agtccatatc ggatagtcat     540
agtcctccgc ctcgtaattc ttgcattctt cttccgcttt cggatcttaa              590

<210> SEQ ID NO 15
<211> LENGTH: 580
<212> TYPE: DNA
<213> ORGANISM: Cucurbita maxima

<400> SEQUENCE: 15
agtttcctca aagattgatg ttatcgatcg taacgacaga tatgctaacc gcaatatcgt      60
gttctttgat atcaacatgc gaggactaga tggaatccaa tgtccagttt atgttggcac     120
gggatgtgtc ttcaacaggg cggctttatt tggatatgaa ccaccggctc tccgtagaaa     180
aggccaaaga tgcatgcga ttgctggcct tcgtggtgta gctgctgctg cggtggttca      240
aggaagtcga agtcgaagaa aaaaggagta aaagtttgc ttggacgcct gttcacaaat     300
aaaaagaaaa tgatgggaa gagttacgta aggaaagggt ctggaccagt ttttgatcta      360
gaagagatag aagaagggtt tgaaggttac gatgagttgg agaagtcgtc actcatgtcg     420
caaaagaatt tcgagaagag attcgggcag tcgccagttt tcattgcttc aaccctcaag     480
gaagatggag gacttccaga agggactaac agcacatcac tggttaaaga agccatccat     540
gttataagct gtggttatga agagaaaaca gaatggggaa                         580

<210> SEQ ID NO 16
<211> LENGTH: 606
<212> TYPE: DNA
<213> ORGANISM: Cucumis sativa

<400> SEQUENCE: 16
gggccggtgt gtcgtatgcc attaacagtg gttaccaatc ttggggtcct cttttttggta     60
agctgttctt tgcattgtgg gttattgtcc atttatatcc tttcctaaag ggtttactgg     120
gaaggcaaaa tcgtacacca accatcgtca ttgtctggtc cattctcctt gcttccattt     180
tctccttgct ttgggtgcga atcgatccat ttacctcggc ctcgacgaag gctgccaatg     240
gtcaatgtgg tatcaattgc tagacagttg catcatagtt ttgttctcgc gaagtggtga     300
ttttcctgtg aatatgacaa gaaagaaatc aaggcatgga gaaaactaaa agagccctca     360
ggaaggaacc acaaatttga agaaaatgag aaatgatatg aggttttttca gattctctca     420
cagtctttta caccagaatt tgtaggtgtc ttgaagttgt attggtaatg ttataatatt     480
atattgtgca gtattgtgaa gttccatttg tttaatgaaa atagataaag gaattattta     540
```

```
tatatcagga gaatttgtaa gaacagacac tgaatttttt gatgtttcag aattgttatg      600
acagtg                                                                606
```

<210> SEQ ID NO 17
<211> LENGTH: 538
<212> TYPE: DNA
<213> ORGANISM: Cucurbita maxima

<400> SEQUENCE: 17

```
ggtccccttt tcggcaaact gttcttcgcg ttctgggtga ttattcatct ctatcccttc       60
ctcaagggtt tgatgggtcg ccagaaccga actcccacga tcgtggttgt ttggtccatc      120
ctccttgcct caattttctc cctttatgg gttcggatcg atcccttcac aactcgggta      180
actggtcctg acgttgaaca atgtggaatc aactgctaaa gagtattgaa caaagcaacg      240
ccctcgaact ggaatctcga agctaatgca ggtacgtacg atcctagctt atcgatcgac      300
aacgcgttta tttaagttta tttggtgctg tgtttgaaag atagattgca gaggttgatg      360
atgatcctct tcaaatttt tggtctcccc cttggtgttc tttgtatgta caaacttgtt      420
attctttctt cccattattt aaggcttctt gtgtactttt gtaagcttta tattgaaaga      480
aatgatattg gaaagtgttt taattaaaaa aaaaaaaaa aaaaaaaaaa aaaaaaa          538
```

<210> SEQ ID NO 18
<211> LENGTH: 388
<212> TYPE: DNA
<213> ORGANISM: Cucurbita maxima

<400> SEQUENCE: 18

```
gggggaacgg gttgttgttt caatcgacaa gctttatatg ttatgatcc ggttctgacc       60 gaggcagatt tggaaccaaa tattataatt aagagttgtt gtggttcaag aaagaagggc      120
aggaacaaga agtacataga caaaagagag gctgcaaaga ggactgagtc taccattcct      180
atctttaata tggaagatat cgaggaaggc gttgaaggtt atgatgatga caggtcgctc      240
ctgatgtccc agaagagttt agagaagcgc tttggccaat ctccagtttt tattgcagcc      300
actttcatgg aaatgggagg tattccacct tcaaccaatc ctgcaactct tctaaaggaa      360
agcattcatg tcatcagttg tgggtatg                                         388
```

<210> SEQ ID NO 19
<211> LENGTH: 453
<212> TYPE: DNA
<213> ORGANISM: Cucurbita maxima
<220> FEATURE:
<221> NAME/KEY: misc_feature
<222> LOCATION: (1)...(453)
<223> OTHER INFORMATION: n = A,T,C or G

<400> SEQUENCE: 19

```
ggggtagcca atgagagtca ccgtgngacc tgcatcatcg atgaaacgtg tagagtttgt       60
ggtgacgaaa ttggactcaa agatgatggg aaagtatttg tggcatgttt ggtgtgtaat      120
ttccctgttt gtcgtccttg ttatgagtac gaaaggagcg aaggcaacaa gtgttgtcca      180
caatgcaaca ctcgctacaa gcgtcataaa ggctcgccta gagtcattgg tgacgacgaa      240
gaagttgacg acgcagacga tttcgacgat gaattcccca tcaaacacca cagtaatgat      300
gagttcgaat caaaacagcc caatccttcg gaacacgata actacaacca gaagaattgg      360
catcaaaacg tccatagttc cttctcagtt gcaggcagtg tgaatgggaa ggagatggag      420
ggcgaaaaaa aaaaaaaaaa aaaaaaaaaa aaa                                   453
```

<210> SEQ ID NO 20
<211> LENGTH: 506
<212> TYPE: DNA
<213> ORGANISM: Cucurbita maxima

<400> SEQUENCE: 20

| | | | | | |
|---|---|---|---|---|---|
| aactccgacg | attgtggttg | tatggtccat | cctccttgcc | tcaatcttct | cccttttatg | 60 |
| ggttcggatt | gatcccttca | caacccgagt | aactggcccc | gacgtcgaac | agtgtggaat | 120 |
| caactgctaa | agggtaaagg | gaatacattt | atacatatga | atgaagatag | aacaacagta | 180 |
| ctctcaaacg | aaaattgatc | cagatcatgc | ggcttctctt | ctgttttcat | ccctgaact | 240 |
| ggaatctcaa | agctcataaa | ggtacaaatc | tagcttatct | atccacaaca | gaatttaaat | 300 |
| taatttattt | ggtgctgtgt | ttctgagttt | gaagttatgg | aagagattca | ttgcagaagt | 360 |
| tgatgatgat | cttcaaattt | ttccccccct | cccactcagt | gttccttctt | gtatgtacaa | 420 |
| ataaaaactg | atgacacatg | atgcttatta | ttttttcttc | tcatgtattg | agtataaact | 480 |
| atgatgttgg | ttctttaaaa | aaaaaa | | | | 506 |

<210> SEQ ID NO 21
<211> LENGTH: 800
<212> TYPE: DNA
<213> ORGANISM: Cucurbita maxima
<220> FEATURE:
<221> NAME/KEY: misc_feature
<222> LOCATION: (1)...(800)
<223> OTHER INFORMATION: n = A,T,C or G

<400> SEQUENCE: 21

| | | | | | |
|---|---|---|---|---|---|
| gtccaagttc | agacaaaccg | attaccattt | atgccctcca | tctctagatt | tgtctatttc | 60 |
| aatcttgctt | ccattcccaa | tttctatctc | tctgcctctt | ccccccttcc | ttatctcttt | 120 |
| cacattgtct | cttcttcttc | atttctgaag | caccgatttg | caacagccat | ggcgtttgca | 180 |
| ggaaccaccc | agaagtgcat | ggcctgcgac | aagactgtct | atttggtcga | caagctcact | 240 |
| gctgacaatc | gtgtctacca | caaagcttgc | ttccgctgcc | accactgcaa | aggaaccctc | 300 |
| aagctaagca | attacaactc | ctttgaaggg | gtgctctatt | gccgcccaca | cttcgatcag | 360 |
| ctctttaaaa | gaactggaag | cttagataaa | agcttcgaag | gaacaccaaa | gattgggaaa | 420 |
| ccggagaaac | cagctgattc | tgagagaccg | acagcgacca | aggttgcaag | catgtttgtc | 480 |
| ggcaccaaag | acaaatgcct | tggctgtaag | aacacagtgt | atccgaccga | gaaggtttca | 540 |
| gtgaatggaa | cctcgtacca | caagagctgc | ttcaagtgct | gccatggcag | atgtacaatc | 600 |
| agcccatcaa | attacattgc | ccatngaagc | cgactntact | gcaaacatca | ccatacccaa | 660 |
| ctcatccatc | accataccca | actcatcaaa | gaaagaggaa | acttgagcca | actggaggga | 720 |
| agccattaaa | ggaccttaag | ctcgtaggcc | cttttatgt | ggctccatac | ctctcctgct | 780 |
| gtttagtcct | gcttttacgc | | | | | 800 |

<210> SEQ ID NO 22
<211> LENGTH: 980
<212> TYPE: DNA
<213> ORGANISM: Cucumis sativa

<400> SEQUENCE: 22

| | | | | | |
|---|---|---|---|---|---|
| gcaatccctt | tacttgtttt | tctcttcttc | cctcgatctt | tcttcctttc | tcctctcgac | 60 |
| cctttcccca | ccttcgattt | ctcccacgaa | ttcgcttctg | ggttctttgt | tttggcccctt | 120 |

-continued

| | |
|---|---|
| ttcgtttaca gatccaccgt tttttccaagt tcttatctca gagaagggaa cttaggtttg | 180 |
| agagttgggg attgcttgtc atcttgattg gttgggtgaa aaagggtcag atctaattcc | 240 |
| aagggcttag ctatgtcttt cattggcaca caacaaaagt gcaaggcctg tgagaagact | 300 |
| gtctaccctg tagagcagct ctctgctgat ggagtttcct accataaatc ttgcttcaaa | 360 |
| tgcagccact gcaaagggac cctaaagctg agcaattatt cttcaatgga aggtgttctg | 420 |
| tattgtaagc ctcattttga gcagctcttc aaagagactg gcaatttcaa caaaaatttc | 480 |
| caatcacctg ccaagtcagc tgagaagtta accccagagc tgactaggtc acctagcaaa | 540 |
| gctgctggca tgttttctgg tactcaagac aaatgtgcta cttgtggcaa aactgtctat | 600 |
| ccattagaga aggtaacagt tgaaagccaa tcctatcaca gtcctgtttt aagtgctct | 660 |
| catggagggt gtgctttatc cccatcaaac tatgcagcat tagagggtat tctatattgc | 720 |
| aaacaccact tctctcagct tttcaaggaa aagggaagct acaaccacct gatcaagtgt | 780 |
| gcatccatga agcgctccgc tgccccggtt cctgaagctt aaagttccaa ttcttatatc | 840 |
| atcatcatca ttcacggttt cggacttaac tctctatttt acatgaatgt gtttaactta | 900 |
| aatttttatg gtattgagat gggaagaag ggtaaaggaa aatatatat gtttaccatc | 960 |
| attcggctca aaaaaaaaa | 980 |

<210> SEQ ID NO 23
<211> LENGTH: 721
<212> TYPE: DNA
<213> ORGANISM: Cucurbita maxima

<400> SEQUENCE: 23

| | |
|---|---|
| agggaaattt gccggacact tagacgacat aaaaaggaga aggagatctt ctgcctcttc | 60 |
| ttcttcccctt cccttccctt cccttccctt cttctcagct tggcagttca gttcagttct | 120 |
| gttctgttct gttcatattc ttccttgaat cctaaagatt ttttgaagat ggcgttttta | 180 |
| gggacaaccc aaaagtgcaa ggcctgtgac aaaactgttt acttggttga tcagctcact | 240 |
| gctgataaca aaatctacca aaggcctgt tcaggtgct accattgcaa gagcactcta | 300 |
| aagttgttca attactcctc ctttgaaggt gtattatatt gcaaacctca ctttgatcag | 360 |
| ttgttcaaga tgactggaag cttggaaaaa agttttgaag gtactccaag aaccattaga | 420 |
| acagacagat ctaccaatca ggtccaatcc aacagcaaag tgtcgagttt atttgctgga | 480 |
| actcaagata aatgtgttac ttgcaagaag actgtttatc caattgagaa ggtggcagta | 540 |
| gatagtaaat cataccacag agcttgcttc aggtgctcac atggaggatg tgtgattagc | 600 |
| ccatcaaact acatagcaca cgaacatcga ctgtactgta ggcatcatca caaccaactc | 660 |
| ttcaaacaga aggggaattt cagccaactt gacaagcatg aagagattaa agggagtgac | 720 |
| t | 721 |

<210> SEQ ID NO 24
<211> LENGTH: 614
<212> TYPE: DNA
<213> ORGANISM: Cucurbita maxima

<400> SEQUENCE: 24

| | |
|---|---|
| gatccctcgt cccttcttcc ctctcgaata tctcttgacg atttcgcttc tgggttctct | 60 |
| gcagatccac ccgcttttca atctctaatc tcagagaata agggacgtta gctgtgagag | 120 |
| ttgtggattg tttgtgatct tgattgggtg aagaaggttc agatctaatc taactcccag | 180 |
| ggcttagcta tgtctttcac tggaacacaa caaaagtgca aggcctgtga agagactgtc | 240 |

```
tatcctgtgg agcagctctc tgctgatgga gtttcctacc ataagtcttg cttcaaatgc    300
agccattgca aaggaactct aaagctgagc aattattgtt caatggaagg tgttctatat    360
tgtaagcctc attttgagca gctcttcaaa gagacaggca acttcaacaa gaacttccaa    420
tcacctgcaa agtcagctga aagactccca gagctgacaa ggtcacctag caaagctgct    480
ggcatgtttt ctggtactca agacaaatgt gctacttgtg gtaaaactgt ttatccactg    540
gagaaggtaa gcacttgaaa ccattcatta tcaacaaaag agcacttaaa actcacaata    600
cttgcaggta acag                                                      614

<210> SEQ ID NO 25
<211> LENGTH: 538
<212> TYPE: DNA
<213> ORGANISM: Cucumis sativa

<400> SEQUENCE: 25
ggtgcaaagc ttgtgacaaa actgtgtacc ctgtagatca gttatctgct gatggagttt    60 cttttccacaa gtcatgtttc aaatgtagcc attgcaaagg aactcttaag ctgagtaatt   120
attcttcaat ggatggtgtt ttgtactgta agcctcattt tgagcagcta ttcaaggaaa    180
ctggcaactt cagcaagaac tttctatctc ctgcaaagtc ctctgagaag ctaactcctg    240
agctgactag gtcgccaagc aaagctgcca gcatgttttc tgggacacaa gaaaaatgtg    300
ctacatgtgg aaaaactgca tatccactgg agaaggttac agttgagagt caagcctatc    360
acaagtcatg ttttaaatgc tcacatggtg gctgttcttt atctccatca aactatgctg    420
cactcgatgg aattttgtac tgcaaacacc acttttcaca gcttttcaag gaaaagggaa    480
gctacaacca tctgataaaa tctgcctcaa tgaagcgtca gcagcgacc tctgatcc     538

<210> SEQ ID NO 26
<211> LENGTH: 380
<212> TYPE: DNA
<213> ORGANISM: Cucurbita maxima

<400> SEQUENCE: 26
cttccatctt cgacgacggc aacaacacc aacacttcgc ttacactgtg caattggtta     60
cctcagcaga tgtgccgatg acactccaag caccttcgag ctcggcttgt gtgagatctt    120
ggccaaggcc ggcgatgggg ccaagctgtc tccgactgag gataaccgct aagataacca    180
cctctaacta tgatgcagcg tcgatgatcg atcggatcct gacgcttatg gcggctcact    240
cggtggtggg atgctctgtg atcatcgatg aaaatgggaa taagcagaga ttgtatagcc    300
ttacgccggt ggctaagtat ttagttcttg atgaagatgg ggtgtcattg ggtgttttgt    360
tatccatgat tcaagataaa                                                380

<210> SEQ ID NO 27
<211> LENGTH: 577
<212> TYPE: DNA
<213> ORGANISM: Cucurbita maxima

<400> SEQUENCE: 27
gggaagatcc gccgtgggga aagaaccgcc acaccgttgc cggaagcgag aatcataaaa    60
cagcgaggct agccatacta gagctcgcaa acatgatcag cgttccgatg tccctcaatg    120
ccgtcgtccg tctcaaaatc gccgacgcta tctggcaagg aggttccaat tttccgctct    180
ctgcttctga gatcctcgca cgcttggttc catccggtgg cgacgccgat aatctcgagc    240
```

```
ggatcctccg tatgctcact agctatggcg ttttcgaaga gcatctcaac cctaactcgt    300
cggaccgccg gtattccctc accgacgtag gaaaaactct ggtcaccgat tccgatggtc    360
tctcttacgc gtcgtacgtg cttcagcatc atcaggacgc gcttatgaga gcgtggccaa    420
gagtgcacga ggctgcgatt gacgctacta cggagccgtt tgtcagagct aatggcgaag    480
cagcgtacag ttactacggg aagaatgagg agatgaactt gttaatgcag agagcgatgg    540
ccggcgtatc agtgccgttc atgaaagctg tattgga                            577

<210> SEQ ID NO 28
<211> LENGTH: 653
<212> TYPE: DNA
<213> ORGANISM: Cucumis sativa

<400> SEQUENCE: 28
gattcaactc aactactcac tctcaaaaca aaggtcgtc ggaaacgaaa cgccccgat      60 ggagcaacac aatacctcca ctaccgccga cagtgaaatc aaaacaaag ccagattagc    120 cattatagag ctcgccaaca tgatcagcgt tcccatgtcc ctcaacgcca tcgtccgcct    180
caacgtcgcc gacgccatct ggcaaaacg ttccaactct cctctctccg catctgagat    240
cctcgctcgc gtggttccgt ccggcggcga cgcccataat ctcgagcgca tcttacgtat    300
gctcactagc tacggtgttt ttgaggaaca tctcagccct aactcatcta accaccggta    360
ttccctcact gacgtcggaa aaactctagt cacggactcc gatggcctct cctacgcgcc    420
gtacgtgctt cagcatcatc aggacgcgct tatgagagcg tggccgcgag tgcacgaggc    480
ggcgattgac tcaacgacgg aaccgttcgt tagagcgaac ggtgaagcgg cgtacagtta    540
ttatgggaag aaaacggaga tgaacgagtt gatgcagaga gcaatggcgg gcgtatcggt    600
gccgttcatg aaggctgtat tggacggcta cgatgggttc aaaggagttg aga          653

<210> SEQ ID NO 29
<211> LENGTH: 994
<212> TYPE: DNA
<213> ORGANISM: Cucumis sativa

<400> SEQUENCE: 29
ggcccaaaac aaacaaacaa agaaaaaaaa agaaacagaa aacaatgtcg ttggggtga     60 gcaatgatga ggaagaagcc cagctattcg ctatgcaact ggctagcgca tcggtgcttc    120
caatggtgct gaagacggcg attgagctgg atttgctgga gatcattggg agaggcgggg    180
agggggctct gttatctcca tcccaaatcg cttcccagct gtctgggctt aaaaaccctg    240
aggcccacgt gatgctagac cgcatgttgc gcctgctggc cagctactcc atcctcactt    300
gctccctcga tcccctcccc gatggctccg tccagaggct ctacgtctc gcccctgtct    360 ccaagttctt gatcaagaat catgacggcg tctctattgc ccctctttgt ctcatgaatc    420
aagacaaggt cctcatggag agctggtacc atttgaaaga tgctgtgcta aaggagggaa    480
ttcctttcaa tagagcctac ggaatgagtg ccttcgaata ccacggaaca gatcccagat    540
tcaacaaggt gtttaacaag ggaatgtccg accattccac cattaccatg aagaagattc    600
tggagaccta caagggtttt gaaggcctta attcagtggt ggatgtcggg ggaggcaccg    660
gagccgtact caacatgatt gtttccaagt accctctat tagaggcatc aacttcgacc    720
tccctcatgt cattcaagat gcccctccct acccaggcgt ggaacatgtt gggggtgaca    780
tgtttgtcag cgttccaaag ggggatgcca ttttcatgaa gtggatctgc cacgattgga    840
gcgaccacca ctgcctcaaa ttcttgaaga attgctacga tgcattgccg gagcacggga    900
```

```
aggtgattgt ggctgaatgc attcttccct tagcacccga cgctagcctc gccaccaaag    960
gagtcattca catcgacctc ataatgctgg ctca                                994
```

```
<210> SEQ ID NO 30
<211> LENGTH: 1245
<212> TYPE: DNA
<213> ORGANISM: Cucumis sativa

<400> SEQUENCE: 30
gcaaaatcat tctcctcccc cagaaaagtt gccacacctc cggctagaaa atggcttcct     60
ccgacaacga caccgccgtc gaacagcaac aacattatgc ttacgcagga cacctcgtta    120
ccttatcagt cctacccatg acactccaag cagtgttcga gcttggtgtg ttcgagatct    180
tggcaaaggc tggggatggg gccaacctct ctccagcaga gatagcggct gagataacca    240
ctacaaaccc caacgcagca ttgatgcttg atcggatgtt gaggcttttg gcatgccact    300
cggtggtggg atgctctata gtttctgata agatgggaa tgtgcaaagg ctttatagcc      360
ttactccgat ttctaaatgt tatgttcgaa atgaagatgg tgtttcgttg ggtccaatgt    420
tatcattgat tcaagataaa gtgtttctgc aaagctggag tgagttgaag aatgcagtaa    480
ctgaaggagg agttccttt gaccgagctc atggaggagt taatgcattt gaatacccta     540
agttagatcc aagattcaac caagtatttta acattgcaat ggtaaatcac actacaatgt   600
ccataaagaa aattgtggaa tcatacaaag gttttgcaaa catcaagcaa ttagttgatg    660
ttggtggtgg ccttggggtc acccttcaaa tcatcacttc tacctatcct tccatcaaag    720
gcatcaattt cgacttacct catgtcatcc gtgatgcccc tgcttataat ggggttcaac    780
atgtgggagg agacatgttt gagagtgttc caaatgcaga tgctatttc atgaagtgga    840 tactacatga ttggagcgac gatcattgca caaagttatt gaaaaattgc tataatgcaa    900
ttccagatga tggaaagata atcatagtag agagtgtgat tcccacgaag cctgaaatca    960
ccaatgtaac aaaggcaaca actcaaggtg atgtgcttat gatgactcaa aatccaggag   1020
gaaaggaaag aactagagat gaatttaaga gcctagcaac caaagctggg tttaaacatg   1080
tcatgttcga atgttttgtt gctaatcttt gggttataga gttacttaaa aattaacttt   1140
tatatattgc atgcaccaaa cttattgatg gtttagttac tactgtattg tcattgaatt   1200
tctatgtttc tatgtttcta tgtccttttg gttgctgaac tttct                   1245
```

```
<210> SEQ ID NO 31
<211> LENGTH: 681
<212> TYPE: DNA
<213> ORGANISM: Cucurbita maxima

<400> SEQUENCE: 31
gctttaacaa ccaagtccag ggagaaagaa tagaaaagaa tggggtcctc ggggaaaggt     60
tgtgaggtcc agatcacccc caccacccga gtgagcgatg aagaagcaca gctgttcgcc    120
atgcagttgg cgagcgcctc ggttcttcca atggtgctga aggccgccat cgagctagac    180
gtgctggaga tcattggggc ggcaggggag ggggctttgt tgtcccctc acaaattgcc      240 tctcacctct cctactccat cctcacttac tccctcaata ctctcccga tggctcactc     300 cagaggctct acggcctcgc ccctgtagcc aagttcttgg tcaagaatca agacggcgtc    360
tccatcgctc ccctgtgtct catgaaccag gacaaggtcc tcatggagag ctggtaccat    420
ttgaaagatg cggtactgga aggaggaatt ccattcaaca aagcatacgg aatgacggcg    480
```

-continued

| | |
|---|---|
| ttcgaatatc atgga acaga tccgagattc aacagggtgt tcaacagggg aatgtccgac | 540 |
| cattccacca ttaccatgaa gaagattcta gagacctaca aaggcttcga aggccttaat | 600 |
| tcactggtgg atgtgggcgg tgggaccgga gctgttctca acatgatagt ctccaagtac | 660 |
| ccttctatta ggggcatcaa c | 681 |

<210> SEQ ID NO 32
<211> LENGTH: 902
<212> TYPE: DNA
<213> ORGANISM: Cucurbita maxima

<400> SEQUENCE: 32

| | |
|---|---|
| gctttaagca aaccaaagtc cagggagaaa gaatagaaaa gaatgggggtc ctcggggaaa | 60 |
| ggttgtgagg tccagatcac ccccaccacc cgagtgagcg atgaagaagc acagctgttc | 120 |
| gccatgcagt tggcgagcgc ctcggttctt ccaatggtgc tgaaggccgc catcgagcta | 180 |
| gacgtgctgg agatcattgg ggcggcaggg gaggggggctt tgttgtcccc ctcacaaatt | 240 |
| gcctctcacc tctccttctc tggggccaaa accccaaacc ctgaggcggg tgtggttcta | 300 |
| gaccgcatgc tccggttgct ggcctcctac tccatcctca cttactccct caatactctc | 360 |
| cccgatggct cactccagag gctctacggc ctcgcccctg tagccaagtt cttggtcaag | 420 |
| aatcaagacg cgtctccat cgctcccctg tgtctcatga accaggacaa ggtcctcatg | 480 |
| gagagctggt accatttgaa agatgcggta ctggaaggag gaattccatt caacaaagca | 540 |
| tacggaatga cggcgttcga atatcatgga acagatccga gattcaacag ggtgttcaac | 600 |
| aggggaatgt ccgaccattc caccattacc atgaagaaga ttctagagac ctacaaaggc | 660 |
| ttcgaaggcc ttaattcagt ggtggatgtg ggcggtggga ccggagctgt tctcaacatg | 720 |
| atagtctcca agtaccccttc tattaggggc atcaacttcg acctccctca tgtcattcag | 780 |
| gacgcccctg cctacccagg cgtccaacat gttgggggag acatgtttgt gagcgtgcca | 840 |
| aagggggatg ctattttcat gaagtggatc tgtcacgatt ggagcgacca gcactgcctg | 900 |
| aa | 902 |

<210> SEQ ID NO 33
<211> LENGTH: 587
<212> TYPE: DNA
<213> ORGANISM: Cucurbita maxima

<400> SEQUENCE: 33

| | |
|---|---|
| agaggaaaca gaggagctgc ttaaaggcca agcagagata ttggaaatat atgctctgtt | 60 |
| ttgctgattc aatggcctta aaatgcgccg tcgagcttca cttagctgat atcatcaact | 120 |
| ctcatgcctc tccctatcg ctatctcaaa ttgcttcctc cattgtcgcc tccgatccct | 180 |
| tagccacccc ggagatctcc tacctcaccc gcatcatgag actgttggtc cgtcggaaca | 240 |
| tcttcgccgt tcatcactca ccagacgcg gagccact ttatgactc acccactcct | 300 |
| ccaaatggct ccttcgtgac gccgagcaca ccctcgctcc gatggtgcta gcggagcttc | 360 |
| acaaatggat ggtcgaccca tggctctgtt tctcccaagg cgttaaagaa ggcggcgacc | 420 |
| aattccaaaa ggccaacggc cttgacattt ggagcttcgc ttccagaaac ccccaattca | 480 |
| accaattgtt catcaacgcc atggcttcca cttccaaagt catcatgaaa gcggttctct | 540 |
| ccgtttacca agatgggttc agctcgattg agtcactaac cgacgtc | 587 |

<210> SEQ ID NO 34
<211> LENGTH: 1025

<210> SEQ ID NO 34
<211> LENGTH: 1025
<212> TYPE: DNA
<213> ORGANISM: Cucurbita maxima

<400> SEQUENCE: 34

| | | | | | |
|---|---|---|---|---|---|
| gtctactctc | actctctaaa | aattatactt | ttccggccac | ctcatggcgg | tctacggcgg | 60 |
| cgacgttccc | caagtggatc | cgagaagcgg | cttctgcaaa | tccacgaaaa | ttttccacag | 120 |
| caaacgccgc | ccaatcccac | ttccccctaa | ccaatccctc | gatgcgacga | cgtttatctc | 180 |
| atcccgcccc | cacaacggca | aaatcgccct | catcgacgcc | accaccggcc | aacacatcac | 240 |
| ctattcccac | ctctgggagt | ctgtcgactc | cgtagcctcc | ttcctttccg | acatgggcat | 300 |
| cagaaaaggc | cacgtcatcc | tcctcctttc | cccaaactcc | attttcttcc | ccattatttg | 360 |
| cctcgccgtc | atgtccctcg | cgccgtcat | aaccaccaca | aatcccctca | acacccctca | 420 |
| agaaatcgcc | aaacagatcg | ccgattccaa | ccccatctta | gccttcacca | cccaacaact | 480 |
| aatccccaaa | atcgccagtt | ccaaattgcc | agtcgttctg | atcgacggtg | aaattcaaat | 540 |
| taaaaaattc | tcagtcaaaa | tcgtgtcgac | gctgagcgaa | atgatgagga | aaaaatccag | 600 |
| tggaagtcga | gttaaggagc | gtgtggacca | aaacgacaca | gcgactctgc | tttactcctc | 660 |
| tggaacgaca | ggggccagca | aggcgtagt | gtcgtctcac | aagaatctaa | ttgcgatggt | 720 |
| tcaagtcgtt | gtgacgaggt | tcaaattgag | cgaaggggaa | gggactttta | tttgtacggt | 780 |
| tccgatgttc | catatttacg | gccttgtggc | tttcgctacg | gggctgctct | cttcgggatc | 840 |
| gacaatcgtc | gtgttgtcga | aattcgagat | tcatgaaatg | ttgtcggcga | ttgagaagta | 900 |
| cagagccacg | tatctgcctc | ttgtgccgcc | gatactggtg | gcgatggtga | acgctgccga | 960 |
| gcagataaag | ggaaagtacg | atttggggtc | gttacacacg | gcgttgtccg | gcggagcgcc | 1020 |
| gctcg | | | | | 1025 |

<210> SEQ ID NO 35
<211> LENGTH: 707
<212> TYPE: DNA
<213> ORGANISM: Cucurbita maxima

<400> SEQUENCE: 35

| | | | | | |
|---|---|---|---|---|---|
| ggtgaatcgg | taaaggttca | tctgttcttc | ttcttcttct | tcttcaatca | actaaaatca | 60 |
| tcgccattga | aatggccaat | gaaacggttc | acgacttcat | tttccggtcg | aaattgccgg | 120 |
| atatctacat | ccctaagcac | ctacctctgc | actcgtactg | ccttcaagaa | aagatggcag | 180 |
| agatcggcca | ccgggacctgt | ctaatcaatg | ccgtcactgg | tgaatccttc | acttattccg | 240 |
| acgtcgacct | cgccgctcgc | aaggccgcct | ccggattgta | caaactcggt | attgcaaaag | 300 |
| gcgatgtgat | catgctcctc | ctcccgaact | caccggaatt | cgtcttcgct | ttcctcggcg | 360 |
| cgtcgtacct | tggcgcgatt | atgacggcgg | cgaatccttt | cttcactgcg | gcagagatcg | 420 |
| caaagcaagc | gaaaggatcg | aaggcgaaat | tgacaatcac | gcaatcgtcg | tattacgaga | 480 |
| aagtgaagga | aataacagag | caattacctg | atgctaaaat | catgaccatc | gattctccgc | 540 |
| cgctaggttg | cttatcgttc | gccgatttaa | tccagggagg | cgatcatgag | attccggcgg | 600 |
| tggagatcag | tcccgacgac | gttgttgctc | tgccgtactc | ctctggaacc | accggattgc | 660 |
| cgaaaggagt | gatgctaaca | cataaaggat | tagtgacgag | tgtggct | | 707 |

<210> SEQ ID NO 36
<211> LENGTH: 650
<212> TYPE: DNA
<213> ORGANISM: Cucurbita maxima -continued

<400> SEQUENCE: 36

```
gtaaaatctt ccattaagag attattcgtt cttcttcatc ttcaaaacac accaaatccg      60
ccattgaaat ggctgttgaa gctcttcaga atgacttcat tttccgctcc aaactgcccg     120
atatttacat tcctaaccac cttcctctgc actcctattg cctacacgaa aacctcgcca     180
aaatcggcca ccggacttgt ctaatcaatg ccgtcactgc cgaatccttt acctaccacg     240
acgtcgacct cgccgcacgc aaggtcgcct cgggattgaa caaactcggc attgcgcaag     300
gcgatgtgat tttgctcctc ctccagaatt cacccgaatt cgtcttcgct ttccttggtg     360
cgtcgtatcg cggcgcgatt atgacagcgg cgaatccttt cttcacgcg gcggagatcg     420 caaagcaagc aaaaggatcg aatgcgaaat taatcgtgac gcaatcgtcg tattatgaaa     480
aagtgaagga ataacagag gaattacctg atgttaaaat catgaccgtc gattctccgc     540
cggatggttg tttatcattc gccgatctaa ttcaggccga cgaacgagag atgccgactg     600
ttgaaatcaa tccggacgat gtggttgcgc tgccgtattc ctctggaacc                650
```

<210> SEQ ID NO 37
<211> LENGTH: 584
<212> TYPE: DNA
<213> ORGANISM: Cucurbita maxima

<400> SEQUENCE: 37

```
ggcaaaacga cacagcaact ctgctttatt cgtctggaac gacaggggcg agcaagggcg      60
tagtgtcgtc tcataaaaat ttaattgcga tggttcaggt ggttgtgacg aggttcagat     120
taagcgaagg ggaagggact tttatctgta cggttccgat gtttcatatc tatggactcg     180
tggccttcgc gacggggctg ctgtcttcag gatccacgat catcgtgttg tccaaattcg     240
aaattcatga gatgttgtct gcgattgaga agtacagggc aacgtatctg ccacttgtgc     300
ccccgattct agtggcgcta gtgaacgccg ccgagcagat aaaggggcaag tacgatttga     360 gctccttgca cacggcgttg tccggcggag cgccgctggg gaaggaggtc attgagggtt     420
ttgttgagaa atatccgaac aggcgatctg tgttacatcg atgaagatgg ttttattttt     480
gtggttgata ggctcaaaga actcatcaaa tacaagggtt atcaggtgcc tccagcagaa     540
ttagaggcgt tgttacttgc acatcctaat atctctgatg cagc                      584
```

<210> SEQ ID NO 38
<211> LENGTH: 495
<212> TYPE: DNA
<213> ORGANISM: Cucurbita maxima

<400> SEQUENCE: 38

```
acaatccgga gcgacagccg ccacaatcga caaggatggg ggttgcacac tggcgacatc      60
ggattcatcg acgacgacga cgagctgttc atcgtcgatc gattgaagga acttataaag     120
tataagggat ttcaagtggc tccggcggaa ttggaagctc tgttgctcac tcatccggca     180
atctctgatg ccgccgtcgt tccaatgaaa gatgaagaag ccggagaggt tccagttgca     240
ttcgtggtga gattgaagaa ctctgaagta actgaagatg aaattaaaca attcatatcg     300
aagcaggtgg ttttctacaa gagaatcaag agggcgttta tgatagacgc aattccgaaa     360
tcgccgtccg gaaagatctt gaggaaggag ttgagggcaa agttggcaac tggttttcca     420
atttctaatt aattattatt cttcctttttc caaattctct cctcccaaaa aaaaaaaaaa     480
aaaaaaaaaa aaaaa                                                      495
```

<210> SEQ ID NO 39
<211> LENGTH: 586
<212> TYPE: DNA
<213> ORGANISM: Cucumis sativa

<400> SEQUENCE: 39

| | |
|---|---|
| gctcctcccg acggttgttt atggtttggt gatctaatta aagccgacga aagagaggtt | 60 |
| ccgagggtgg atatcgaccc agaagacgtg gttgcgctgc cgtattcgtc gggaacgacg | 120 |
| ggattgccga agggagtgat gcttacacat aaaagtttgg ttacgagtgt ggctcagcaa | 180 |
| gtggatgggg aaaatccaaa tctgtattat ggacatgagg acgtgattct gtgtgttctg | 240 |
| ccgttgtttc atatttattc tttgaattcg gttttgctgt gtggattaag agctggaagt | 300 |
| accattttga ttatgcccaa atttgagatc ggtttgcttt tgcaattggc ggagaaatat | 360 |
| ggagttaccg ttgcgcccat cgtgccgccc atcgtactgg ctattgcaaa gtcaccggag | 420 |
| cttgagaagt atgacctttc gtcaatcaga attattaaat ccggcggtgc tccgcttggg | 480 |
| aaggagcttg aagataccgt gagagccaag tttcctaagg ctgtgctcgg acagggatat | 540 |
| ggaatgacgg aggcgggtcc agttcctaca atgggattgg catttg | 586 |

<210> SEQ ID NO 40
<211> LENGTH: 374
<212> TYPE: DNA
<213> ORGANISM: Cucurbita maxima

<400> SEQUENCE: 40

| | |
|---|---|
| ggatttgtcg tctatcagaa tgattaaatc tggaggagct ccgctcggga aggagcttga | 60 |
| agataccgtg agagccaagt ttcccaaggc tgtgctcggc cagggatatg gaatgacaga | 120 |
| ggcgggacct gtactaacga tgggtttagc atttgcaaag gagccatttc cgatgaaacc | 180 |
| aggagcctgc ggcaccgtcg tgagaaatgc cgagataaag atcgtcgata ccgaaaacgg | 240 |
| cggctcgttg ccccgaaaca cgccgggaga gatctgcatc aaaggcgatc aaatcatgaa | 300 |
| aggctatctg aacaatccgg aggcaacggc tgctacaatc gacaacgaag ctggttgca | 360 |
| caccggcgat atcg | 374 |

<210> SEQ ID NO 41
<211> LENGTH: 1002
<212> TYPE: DNA
<213> ORGANISM: Cucurbita maxima

<400> SEQUENCE: 41

| | |
|---|---|
| ggatttgtcg tctatcagaa tgattaaatc tggaggagct ccgctcggga aggagcttga | 60 |
| agataccgtg agagccaagt ttcccaaggc tgtgctcggc cagggatatg gaatgacaga | 120 |
| ggcgggacct gtactaacga tgggtttagc atttgcaaag gagccatttc cgatgaaacc | 180 |
| aggagcctgc ggcaccgtcg tgagaaatgc cgagataaag atcgtcgata ccgaaaacgg | 240 |
| cggctcgttg ccccgaaaca cgccgggaga gatctgcatc aaaggcgatc aaatcatgaa | 300 |
| aggctatctg aacaatccgg aggcaacggc tgctacaatc gacaacgaag ctggttgat | 360 |
| aacattggat cagaagacta atggagacga aaatggcaca tatctgaact ttttgccgat | 420 |
| gtttcatgtg tttggattgg tttgtataac atgtgcgcag ctgcagagag gaaacaccat | 480 |
| tgtctctatg ccaaagttta acctggagaa ggcccctttgg gcagtggaga agtacaaggt | 540 |
| gacagatcta tgggttgtgc cgcctgttgt gcttgctttg gcaaagcaaa gtgtggtaaa | 600 |
| gaaatacaac ctttcatccc tgaagcatat cggttcaggg gctgcacctc ttgggaagga | 660 |

-continued

| | |
|---|---|
| attaatggat gaatgtgcta acaacattcc cagtgctgtg gttctccagg gttatggtat | 720 |
| gactgagact tgtggagttg tttctttgga gaatcgagca gttggcaaac gaaatacagg | 780 |
| ttcggctgga acacttgcct ctggtgttga ggctcaaata gtcagcgtag atactttgaa | 840 |
| gcctcttcct cctaatcaat atggagagat actggttcgg ggaccgaata tgatgcttgg | 900 |
| ttacttaaac aatccacagg ccaccaagca aactattgac aaatatggct gggtgcatac | 960 |
| tggagacctt ggatactttg atgaagcaca ccggcgatat cg | 1002 |

<210> SEQ ID NO 42
<211> LENGTH: 626
<212> TYPE: DNA
<213> ORGANISM: Cucurbita maxima

<400> SEQUENCE: 42

| | |
|---|---|
| ggttgtgacg aggttcagat taagcgaagg ggaagggact tttatctgta cggttccgat | 60 |
| gtttcatatc tatggactcg tggccttcgc gacgggctg ctgtcttcag gatccacgat | 120 |
| catcgtgttg tccaaattcg aaattcatga gatgttgtct gcgattgaga agtacagggc | 180 |
| aacgtatctg ccacttgtgc ccccgattct agtggcgcta gtaacgccg ccgagcagat | 240 |
| aaagggcaag tacgatttga gctccttgca cacggcgttg tccggcggag cgccgctggg | 300 |
| gaaggaggtc attgagggtt ttgttgagaa atatccgaac gttgcgattc ttcagggta | 360 |
| tgggttgacg gagtccaccg gaataggagc ttccactgat tctctggagg agagccgccg | 420 |
| gtatggcacg gcggggcttt tgtctccgag caccgaggca atgattgttg acccggaaac | 480 |
| tggcgaggct ctgcccgtga accggaccgg agagctttgg ctcagaggac ccaccgttat | 540 |
| gaaagggtat tttggtaatg tggaggccac agcctcaacg ctcgactcga tgggatggtt | 600 |
| gagaacaggc gatctgtgtt acatcg | 626 |

<210> SEQ ID NO 43
<211> LENGTH: 618
<212> TYPE: DNA
<213> ORGANISM: Cucumis sativa

<400> SEQUENCE: 43

| | |
|---|---|
| aaccaaatct ttgaatcccc catatcccaa cccatcctct ttcttcaatc ccattttggc | 60 |
| aatggatatc acgatgaaca aatctttcaa tccccaatcg caagtttaca cttcccgtcg | 120 |
| tcctccaatc cactttccga ccgacccac aatctccatt gtttcattcc tctttcgaaa | 180 |
| ctcctcttct tatcccaacg cccttgccct tgtcgacgct gactccggcg aatccctcac | 240 |
| tttccgtcag cttcaaatcc aagtctccaa gctcgctcat gtgttcatcc aactcgggat | 300 |
| tcaaaaaggc gatgtggttc tcatattcgc gcccaattcc attcacttcc ttgtttgttt | 360 |
| cttcgccatc gtcgccatcg gagccattgc caccacttgt aatcctgctt acacttccgc | 420 |
| tgaactgtca aaacaagtcg ctaactgcaa acctaagctc gtaatcaccg ttcccgaact | 480 |
| ctgggacgta atcggtaaac tcaacttacc ttctataatt ctgggttcta aaatttcttc | 540 |
| aaaattttcc cgttccaaca tctgggctta ctccgatttg attaaaaaag ccggcgatgt | 600 |
| gtccaatttg ccggtgag | 618 |

<210> SEQ ID NO 44
<211> LENGTH: 372
<212> TYPE: DNA
<213> ORGANISM: Cucurbita maxima

<400> SEQUENCE: 44

```
gattctgtac tcgtcaggga ctaccgggcg agtgaaagga gtcttactgt ctcacaggaa    60
cctcatagcg tcgatctcta gtgttatgac attagaggcg acggccgacg aaagagagac   120
ggagccgcat cccgtttctc tgtacctgtt acctatgttc catgttttcg gattctatat   180
gatgattcga tcgatttcag aaggccatac gctggttctg atgcgaaagt tcggtttcga   240
ggaaatgtta agagccgtgg agaagtatag ggttacatac ataccggttt ctcccccgct   300
ggtggtggcg atggttaagt cggagctggt ggccaagtac gatcttagct ctcttcaaat   360
tttgggatgc gg                                                       372
```

<210> SEQ ID NO 45
<211> LENGTH: 581
<212> TYPE: DNA
<213> ORGANISM: Cucumis sativa

<400> SEQUENCE: 45

```
ggtttcttct tctttttgtaa acttggtaat tgaaataaaa gaaccatctt caaattatat    60
ccatcacaga agtggacaca aaacccgttt tgtgggcaca gccacaagcc gggtcgctct   120
cggagctgtc aacccgaaga cgtcgctcat gtccatttcg cttggcttca tcccatccgg   180
caattcccaa tcgaaacagt gcaacaagtg ggccaccgca atctcaagtc cgtatagacc   240
cagctgcatc cctgggcaag accgccttcc cgatccgaac ggaatgaact cgaagttgtt   300
cccttttgaaa tctgggactc cttcttctag aaacctggcc ggccggaatg tctcggcgtc   360
gtcccatgag gccggatccc tcccgatggc ccacgcgttc accatgattc gagattttgc   420
cggaatgaag tagccggcga tgaccgcgtc ctccgctgcc tcgtggagga ggagtgggat   480
cggcgggtgc agccggatgg tctccttgag acagcacttt aagaaagtca agttgtcgag   540
gtcggtttct tcgacacgtc gttggagacc aacgacttgg g                       581
```

<210> SEQ ID NO 46
<211> LENGTH: 696
<212> TYPE: DNA
<213> ORGANISM: Cucurbita maxima

<400> SEQUENCE: 46

```
ggagacgtgc ggagctcact ggaaagagaa aaggtaaaga aatattcaaa ggaagttcaa    60
taatctccgg aaatggcgtc caccaacaac acaccagaaa accagaacca agccggaagg   120
caccaggaag tcggccacaa gagcctcttg cagagcgatg ctctgtatca gtacattctt   180
gagacgagcg tttatccaag agagcctgaa tcgatgaagg aattgagaga attgactgcc   240
aaacatccat ggaacatcat gactacatcg gcggacgaag gacagttctt aaacatgctt   300
ttgaaactaa ttaatgcgaa gaaaacgatg gagattggag tatacactgg ctactctctt   360
ctcgctacag ccctagcact tccggaagac ggacagattc tggctatgga tattaacaga   420
gaaaattacg agctcggttt accggtgatt gagaaagccg gcgttgctca agatcgag     480
ttcaaggaag gccccgcgct ccctgttctt gacgagatgg tggctgatga aaaaatcat    540
ggaagctatg acttcatttt tgtggatgct gataaagaca actacataaa ttatcataag   600
agattgatag atttggtgaa agttggagga ttgattgggt acgacaacac gctatggaat   660
ggatcggtgg ttgctccacc cgacgcccca ctacgc                             696
```

<210> SEQ ID NO 47
<211> LENGTH: 609
<212> TYPE: DNA

<213> ORGANISM: Cucurbita maxima

<400> SEQUENCE: 47

```
agattctggc tatggatatt aacagagaaa attacgagct cggtttaccg gtgattgaga      60
aagccggcgt tgctcacaag atcgagttca aggaaggccc cgcgctccct gttcttgacg     120
agatggtggc tgatgtaaga ttttttttt tttctttttt tcttccctaa gtgaaatttg     180
aagaatcaat taggtgagct ttaaaatgat aactgtttta ggagaaaaat catggaagct     240
atgacttcat ttttgtggat gctgataaag acaactacat aaattatcat aagagattga     300
tagatttggt gaaagttgga ggattgattg ggtacgacaa cacgctatgg aatggatcgg     360
tggttgctcc acccgacgcc ccactacgca agtatgttag gtactacagg gactttgtgt     420
tggagctcaa caaagctctt gctgctgatc caaggatcga gatttgtatg ctccctgttg     480
gtgatggaat cactctctgt cgtcggatca actgaacaca ttaacgtttc atgcactctc     540
acttacgcaa ttgttcttct tcattgcttg cctccctctc ttttttaatat cgatttcctt     600
cgagttttt                                                              609
```

<210> SEQ ID NO 48
<211> LENGTH: 312
<212> TYPE: DNA
<213> ORGANISM: Cucumis sativa

<400> SEQUENCE: 48

```
gctctcacgc cttcattcca agcatccaat ccaaccacct tcgtttcagt tcaaccaaat      60
aatggcaaac tatcactccg acaagaacat cctcaagagc accgctcttc tccagtatat     120
tctgaaagcc aacgcctatc cgagggagca cgaacagttg aaggaactca gggaatcgac     180
gttcaataaa tttgataagt ccgggagtgt gatgaatgta ccggtggatg aaggattgtt     240
tctatcaatg cttttgaaat tgatgaatgc aaagaaaacg atagaggtcg gcgtgtacac     300
tggctattcg ct                                                          312
```

<210> SEQ ID NO 49
<211> LENGTH: 136
<212> TYPE: PRT
<213> ORGANISM: Cucurbita maxima

<400> SEQUENCE: 49

```
Met Glu Val Asp Ala Asn Ser Gly Lys Ser Ser Lys Gln Ile Gly Ser
 1               5                  10                  15
Gly Gln Val Cys Gln Ile Cys Ser Asp Ser Val Gly Thr Thr Ala Asp
                20                  25                  30
Gly Glu Pro Phe Val Ala Cys Asp Val Cys Ala Phe Pro Val Cys Arg
            35                  40                  45
Pro Cys Tyr Glu Tyr Glu Arg Lys Asp Gly Asn Gln Ser Cys Pro Gln
        50                  55                  60
Cys Lys Thr Lys Tyr Lys Trp His Lys Gly Ser Pro Pro Val Asn Gly
    65                  70                  75                  80
Glu Ala Val Glu Asp Gly Asp Gly Asn Gly Val Thr Gly Ala Gln Glu
                85                  90                  95
Arg His His Lys Leu Pro Glu Arg Thr Leu Ser Trp Asp Thr Asn Tyr
               100                 105                 110
Asp Lys Glu Gly Ser Phe Asn His Ile Pro Leu Leu Thr Thr Gly Arg
           115                 120                 125
Ser Val Ser Gly Glu Leu Ser Ala
       130                 135
```

-continued

```
                130                 135

<210> SEQ ID NO 50
<211> LENGTH: 224
<212> TYPE: PRT
<213> ORGANISM: Cucurbita maxima

<400> SEQUENCE: 50

Asp Gly Ser Ala Met Leu Thr Phe Glu Ser Leu Ser Glu Thr Ala Glu
 1               5                   10                  15

Phe Ala Arg Lys Trp Val Pro Phe Cys Lys Lys His Ser Ile Glu Pro
            20                  25                  30

Arg Ala Pro Glu Phe Tyr Phe Ala Gln Lys Ile Asp Tyr Leu Lys Asp
        35                  40                  45

Lys Ile Lys Pro Ser Phe Val Lys Glu Arg Arg Ala Met Lys Arg Glu
    50                  55                  60

Tyr Glu Glu Phe Lys Ile Arg Ile Asn Ala Leu Val Ala Lys Ala Gln
65                  70                  75                  80

Lys Met Pro Glu Glu Gly Trp Thr Met Gln Asp Gly Thr Pro Trp Pro
                85                  90                  95

Gly Asn Asn Pro Arg Asp His Pro Gly Met Ile Gln Val Phe Leu Gly
            100                 105                 110

His Ser Gly Gly Leu Asp Thr Asp Gly Asn Glu Leu Pro Arg Leu Val
        115                 120                 125

Tyr Val Ser Arg Glu Lys Arg Pro Gly Phe Gln His His Lys Lys Ala
    130                 135                 140

Gly Ala Met Asn Ala Leu Ile Arg Val Ser Ala Val Leu Thr Asn Gly
145                 150                 155                 160

Ala Tyr Leu Leu Asn Val Asp Cys Asp His Tyr Phe Asn Asn Ser Lys
                165                 170                 175

Ala Leu Lys Glu Ala Met Cys Phe Met Met Asp Pro Ala Tyr Gly Lys
            180                 185                 190

Lys Thr Cys Tyr Val Gln Phe Pro Gln Arg Phe Asp Gly Ile Asp Leu
        195                 200                 205

His Asp Arg Tyr Ala Asn Arg Asn Ile Val Phe Phe Asp Ile Asn Leu
    210                 215                 220

<210> SEQ ID NO 51
<211> LENGTH: 225
<212> TYPE: PRT
<213> ORGANISM: Cucurbita maxima

<400> SEQUENCE: 51

Gly Glu Thr Tyr Leu Asp Arg Leu Ser Leu Arg Tyr Glu Lys Asp Gly
 1               5                   10                  15

Lys Pro Ser Glu Leu Ala Ser Ile Asp Ile Tyr Val Ser Thr Val Asp
            20                  25                  30

Pro Leu Lys Glu Pro Pro Leu Ile Thr Ala Asn Thr Val Leu Ser Ile
        35                  40                  45

Leu Ala Val Asp Tyr Pro Val Asp Lys Val Ser Cys Tyr Val Ser Asp
    50                  55                  60

Asp Gly Ala Ala Met Leu Thr Phe Glu Ala Leu Ser Glu Thr Ser Glu
65                  70                  75                  80

Phe Ala Arg Lys Trp Val Pro Phe Cys Lys Lys Phe Asn Ile Glu Pro
                85                  90                  95

Arg Ala Pro Glu Trp Tyr Phe Ala Leu Lys Val Asp Tyr Leu Lys Asp
```

```
                   100                 105                 110
Lys Val Asp Pro Thr Phe Ile Arg Glu Arg Ala Met Lys Arg Asp
            115                 120                 125
Tyr Glu Glu Phe Lys Val Arg Ile Asn Gly Leu Val Ala Met Ala Gln
        130                 135                 140
Lys Val Pro Glu Asp Gly Trp Thr Met Gln Asp Gly Thr Pro Trp Pro
145                 150                 155                 160
Gly Asn Asn Val Arg Asp His Pro Gly Met Ile Gln Val Phe Leu Gly
                165                 170                 175
Ser Asn Gly Val Arg Asp Leu Glu Gly Asn Glu Leu Pro Arg Leu Val
            180                 185                 190
Tyr Val Ser Arg Glu Lys Arg Pro Gly Phe Asp His His Lys Lys Ala
                195                 200                 205
Gly Ala Met Asn Ala Leu Val Arg Val Ser Ala Ile Ile Ser Asn Ala
        210                 215                 220
Pro
225

<210> SEQ ID NO 52
<211> LENGTH: 223
<212> TYPE: PRT
<213> ORGANISM: Cucumis sativa

<400> SEQUENCE: 52

His Glu Ala Val Asp Tyr Pro Val Asp Lys Val Ser Cys Tyr Val Ser
  1               5                  10                  15
Asp Asp Gly Ser Ala Met Leu Thr Phe Glu Ala Leu Ser Glu Thr Ala
            20                  25                  30
Glu Phe Ala Arg Lys Trp Val Pro Phe Cys Lys Lys His Asn Ile Glu
        35                  40                  45
Pro Arg Ala Pro Glu Phe Tyr Phe Ala Gln Lys Ile Asp Tyr Leu Lys
    50                  55                  60
Asp Lys Ile Lys Pro Ser Phe Val Lys Glu Arg Arg Ala Met Lys Arg
65                  70                  75                  80
Glu Tyr Glu Glu Phe Lys Val Arg Ile Asn Ala Leu Val Ala Lys Ala
                85                  90                  95
Gln Lys Met Pro Glu Glu Gly Trp Thr Met Gln Asp Gly Thr Ala Trp
            100                 105                 110
Pro Gly Asn Asn Pro Arg Asp His Pro Gly Met Ile Gln Val Phe Leu
        115                 120                 125
Gly His Ser Gly Gly Leu Asp Thr Asp Gly Asn Glu Leu Pro Arg Leu
    130                 135                 140
Val Tyr Val Ser Arg Glu Lys Arg Pro Gly Phe Gln His His Lys Lys
145                 150                 155                 160
Ala Gly Ala Met Asn Ala Leu Ile Arg Val Ser Ala Val Leu Thr Asn
                165                 170                 175
Gly Ala Tyr Leu Leu Asn Val Asp Cys Asp His Tyr Phe Asn Asn Ser
            180                 185                 190
Lys Ala Leu Lys Glu Ala Met Cys Phe Met Met Asp Pro Ala Tyr Gly
        195                 200                 205
Lys Lys Thr Cys Tyr Val Gln Phe Pro Gln Arg Phe Asp Gly Ile
    210                 215                 220

<210> SEQ ID NO 53
<211> LENGTH: 211
```

```
<212> TYPE: PRT
<213> ORGANISM: Cucumis sativa

<400> SEQUENCE: 53

Leu Phe Ser Arg His Cys Pro Val Trp Tyr Gly Tyr Gly Arg Leu
 1               5                  10                  15

Lys Trp Leu Glu Arg Phe Ala Tyr Val Asn Thr Thr Ile Tyr Pro Ile
                 20                  25                  30

Thr Ser Ile Pro Leu Leu Ala Tyr Cys Thr Leu Pro Ala Ile Cys Leu
             35                  40                  45

Leu Thr Gly Lys Phe Ile Ile Pro Gln Ile Ser Asn Leu Ala Ser Ile
 50                  55                  60

Trp Phe Ile Ser Leu Phe Leu Ser Ile Phe Ala Thr Gly Ile Leu Glu
65                  70                  75                  80

Met Arg Trp Ser Gly Val Gly Ile Asp Glu Trp Trp Arg Asn Glu Gln
                 85                  90                  95

Phe Trp Val Ile Gly Gly Val Ser Ala His Leu Phe Ala Val Phe Gln
                100                 105                 110

Gly Leu Leu Lys Val Leu Ala Gly Ile Asp Thr Asn Phe Thr Val Thr
                115                 120                 125

Ser Lys Ala Ser Asp Glu Asp Gly Asp Phe Ala Glu Leu Tyr Met Phe
130                 135                 140

Lys Trp Thr Thr Leu Leu Ile Pro Pro Thr Thr Leu Leu Ile Ile Asn
145                 150                 155                 160

Ile Val Gly Val Val Ala Gly Ile Ser Tyr Ala Ile Asn Ser Gly Tyr
                165                 170                 175

Gln Ser Trp Gly Pro Leu Phe Gly Lys Leu Phe Phe Ala Phe Trp Val
                180                 185                 190

Ile Ile His Leu Tyr Pro Phe Leu Lys Gly Leu Met Gly Arg Gln Asn
                195                 200                 205

Arg Thr Pro
    210

<210> SEQ ID NO 54
<211> LENGTH: 199
<212> TYPE: PRT
<213> ORGANISM: Cucurbita maxima

<400> SEQUENCE: 54

Arg Gly Trp Arg Ser Ile Tyr Cys Ile Pro Glu Arg Pro Ala Phe Lys
 1               5                  10                  15

Gly Ser Ala Pro Ile Asn Leu Ser Asp Arg Leu Asn Gln Val Leu Arg
                 20                  25                  30

Trp Ala Leu Gly Ser Val Glu Ile Leu Phe Ser Arg His Cys Pro Met
             35                  40                  45

Trp Tyr Gly Tyr Gly Gly Arg Leu Lys Trp Leu Glu Arg Phe Ala Tyr
 50                  55                  60

Val Asn Thr Thr Ile Tyr Pro Ile Thr Ser Ile Pro Leu Leu Ala Tyr
65                  70                  75                  80

Cys Thr Leu Pro Ala Ile Cys Leu Leu Thr Gly Lys Phe Ile Ile Pro
                 85                  90                  95

Gln Ile Ser Asn Leu Ala Ser Ile Trp Phe Ile Ser Leu Phe Leu Ser
                100                 105                 110

Ile Phe Ala Thr Gly Ile Leu Glu Met Arg Trp Ser Gly Val Gly Ile
                115                 120                 125
```

```
Asp Glu Trp Trp Arg Asn Glu Gln Phe Trp Val Ile Gly Gly Val Ser
        130                 135                 140

Ala His Leu Phe Ala Val Phe Gln Gly Leu Leu Lys Val Leu Ala Gly
145                 150                 155                 160

Ile Asp Thr Asn Phe Thr Val Thr Ser Lys Ala Ser Asp Glu Asp Gly
                165                 170                 175

Asp Phe Ala Glu Leu Tyr Leu Phe Lys Trp Thr Thr Leu Leu Ile Pro
            180                 185                 190

Pro Thr Thr Leu Leu Ile Ile
        195
```

<210> SEQ ID NO 55
<211> LENGTH: 225
<212> TYPE: PRT
<213> ORGANISM: Cucurbita maxima

<400> SEQUENCE: 55

```
Gln Gly Pro Val Tyr Val Gly Thr Gly Cys Val Phe Asn Arg Thr Ala
1               5                   10                  15

Leu Tyr Gly Tyr Glu Pro Pro Leu Lys Pro Lys His Lys Lys Pro Gly
            20                  25                  30

Val Phe Ser Ser Cys Phe Gly Lys Ser Lys Lys Lys Ser Ser Lys Ser
        35                  40                  45

Lys Arg Lys Asp Ser Asp Lys Lys Gln Ser Asn Lys Asn Val Asp Pro
50                  55                  60

Thr Val Pro Ile Phe Asn Leu Glu Asp Ile Glu Glu Gly Val Glu Gly
65                  70                  75                  80

Ala Gly Phe Asp Asp Glu Lys Ser Leu Leu Met Ser Gln Met Ser Leu
                85                  90                  95

Glu Lys Arg Phe Gly Gln Ser Ala Val Phe Ala Ser Thr Leu Met
            100                 105                 110

Glu Asn Gly Gly Val Pro Gln Ser Ala Thr Pro Glu Ser Leu Leu Lys
        115                 120                 125

Glu Ala Ile His Val Ile Ser Cys Gly Tyr Glu Asp Lys Thr Asp Trp
130                 135                 140

Gly Ser Glu Ile Gly Trp Ile Tyr Gly Ser Val Thr Glu Asp Ile Leu
145                 150                 155                 160

Thr Gly Phe Lys Met His Ala Arg Gly Trp Arg Ser Ile Tyr Cys Ile
                165                 170                 175

Pro Asp Arg Pro Ala Phe Lys Gly Ser Ala Pro Ile Asn Leu Ser Asp
            180                 185                 190

Arg Leu Asn Gln Val Leu Arg Trp Ala Leu Gly Ser Val Glu Ile Leu
        195                 200                 205

Phe Ser Arg His Cys Pro Met Trp Tyr Gly Tyr Ser Gly Arg Leu Lys
210                 215                 220

Trp
225
```

<210> SEQ ID NO 56
<211> LENGTH: 245
<212> TYPE: PRT
<213> ORGANISM: Cucumis sativa

<400> SEQUENCE: 56

```
Val Gln Val Phe Leu Gly Gln Asn Gly Val Arg Asp Leu Glu Gly Asn
1               5                   10                  15
```

```
Glu Leu Pro Arg Leu Val Tyr Val Ser Arg Glu Lys Arg Pro Gly Phe
            20                  25                  30

Asp His His Lys Lys Ala Gly Ala Met Asn Ala Leu Val Arg Val Ser
        35                  40                  45

Ala Ile Ile Ser Asn Ala Pro Tyr Ile Leu Asn Val Asp Cys Asp His
    50                  55                  60

Tyr Ile Asn Asn Ser Lys Ala Leu Arg Glu Ala Met Cys Phe Met Met
65                  70                  75                  80

Asp Pro Ile Ser Gly Lys Arg Ile Cys Tyr Val Gln Phe Pro Gln Arg
                85                  90                  95

Phe Asp Gly Ile Asp Arg His Asp Arg Tyr Ser Asn Arg Asn Val Val
            100                 105                 110

Phe Phe Asp Ile Asn Met Lys Gly Leu Asp Gly Ile Gln Gly Pro Ile
            115                 120                 125

Tyr Val Gly Thr Gly Cys Val Phe Arg Arg Gln Ala Leu Tyr Gly Tyr
        130                 135                 140

Asp Ala Pro Ala Lys Lys Lys Ala Pro Arg Arg Thr Cys Asn Cys Leu
145                 150                 155                 160

Pro Lys Trp Cys Cys Cys Cys Gly Thr Arg Lys Lys Thr Lys Thr
                165                 170                 175

Lys Thr Ser Asp Lys Lys Lys Leu Lys Thr Lys Asp Thr Ser Lys Gln
            180                 185                 190

Ile His Ala Leu Glu Asn Ile Glu Glu Gly Ile Glu Gly Ile Asp Asn
        195                 200                 205

Glu Lys Ser Ser Leu Met Pro Gln Val Lys Phe Glu Lys Lys Phe Gly
    210                 215                 220

Gln Ser Pro Ala Phe Ile Ala Ser Thr Leu Met Glu Asp Gly Gly Val
225                 230                 235                 240

Pro Gly Gly Gly Thr
                245

<210> SEQ ID NO 57
<211> LENGTH: 177
<212> TYPE: PRT
<213> ORGANISM: Cucumis sativa

<400> SEQUENCE: 57

Val Val Ile Asp Asp Ser Leu Leu Asn Asp Glu Ala Arg Gln Pro Leu
1               5                   10                  15

Ser Arg Lys Val Ser Ile Pro Ser Arg Ile Asn Pro Tyr Arg Met
            20                  25                  30

Val Ile Val Leu Arg Leu Ile Ile Leu Cys Ile Phe Leu His Tyr Arg
        35                  40                  45

Ile Thr Asn Pro Val Pro Asn Ala Phe Ala Leu Trp Leu Ile Ser Val
    50                  55                  60

Ile Cys Glu Ile Trp Phe Ala Ile Ser Trp Ile Leu Asp Gln Phe Pro
65                  70                  75                  80

Lys Trp Leu Pro Val Asn Arg Glu Thr Tyr Leu Asp Arg Leu Ala Leu
                85                  90                  95

Arg Tyr Asp Arg Glu Gly Glu Pro Ser Gln Leu Ala Ala Val Asp Ile
            100                 105                 110

Phe Val Ser Thr Val Asp Pro Leu Lys Glu Pro Pro Leu Val Thr Ala
            115                 120                 125

Asn Thr Val Leu Ser Ile Leu Ser Val Asp Tyr Pro Val Asp Lys Val
        130                 135                 140
```

-continued

```
Ser Cys Tyr Val Ser Asp Asp Gly Ala Ala Met Leu Thr Phe Glu Ala
145                 150                 155                 160

Leu Ser Glu Thr Ser Glu Phe Ala Arg Lys Trp Val Pro Phe Cys Lys
                165                 170                 175

Lys
```

<210> SEQ ID NO 58
<211> LENGTH: 184
<212> TYPE: PRT
<213> ORGANISM: Cucumis sativa

<400> SEQUENCE: 58

```
Ala Gly Val Phe Ser Ser Cys Phe Gly Lys Ser Lys Lys Ser Ser
1               5                   10                  15

Lys Ser Lys Arg Lys Asp Ser Asp Lys Lys Gln Ser Ser Lys Asn Val
                20                  25                  30

Asp Pro Thr Val Pro Ile Phe Asn Leu Glu Asp Ile Glu Glu Gly Val
            35                  40                  45

Glu Gly Ala Gly Phe Asp Asp Glu Lys Ser Leu Leu Met Ser Gln Met
    50                  55                  60

Ser Leu Glu Lys Arg Phe Gly Gln Ser Ala Val Phe Val Ala Ser Thr
65                  70                  75                  80

Leu Met Glu Asn Gly Gly Val Pro Gln Ser Ala Thr Pro Glu Ser Leu
                85                  90                  95

Leu Lys Glu Ala Ile His Val Ile Ser Cys Gly Tyr Glu Asp Lys Thr
            100                 105                 110

Asp Trp Gly Ser Glu Ile Gly Trp Ile Tyr Gly Ser Val Thr Glu Asp
        115                 120                 125

Ile Leu Thr Gly Phe Lys Met His Ala Arg Gly Trp Arg Ser Ile Tyr
130                 135                 140

Cys Ile Pro Asp Arg Pro Ala Phe Lys Gly Ser Ala Pro Ile Asn Leu
145                 150                 155                 160

Ser Asp Arg Leu Asn Gln Val Leu Arg Trp Ala Leu Gly Ser Val Glu
                165                 170                 175

Ile Leu Phe Ser Arg His Cys Pro
            180
```

<210> SEQ ID NO 59
<211> LENGTH: 134
<212> TYPE: PRT
<213> ORGANISM: Cucumis sativa

<400> SEQUENCE: 59

```
Gly Gly Val Pro Gly Gly Gly Thr Ser Ala Ser Leu Leu Lys Glu Ala
1               5                   10                  15

Ile His Val Ile Ser Cys Arg Tyr Glu Asp Lys Ser Glu Trp Gly Lys
                20                  25                  30

Glu Val Gly Trp Ile Tyr Gly Ser Val Thr Glu Asp Ile Leu Thr Gly
            35                  40                  45

Phe Lys Met His Cys His Gly Trp Arg Ser Val Tyr Cys Ile Pro Lys
    50                  55                  60

Arg Ala Ala Phe Lys Gly Ser Ala Pro Ile Asn Leu Ser Asp Arg Leu
65                  70                  75                  80

His Gln Val Leu Arg Trp Ala Leu Gly Ser Val Glu Ile Leu Leu Ser
                85                  90                  95
```

```
Arg His Cys Pro Ile Trp Tyr Gly Tyr Gly Cys Gly Leu Lys Trp Leu
                100                 105                 110

Glu Arg Phe Ser Tyr Ile Asn Ser Val Val Tyr Pro Leu Thr Ser Val
            115                 120                 125

Pro Leu Ile Ala Tyr Cys
        130

<210> SEQ ID NO 60
<211> LENGTH: 134
<212> TYPE: PRT
<213> ORGANISM: Cucumis sativa

<400> SEQUENCE: 60

Val Ala Gly Val Asn Thr Asn Phe Thr Val Thr Ser Lys Gly Gly Asp
  1               5                  10                  15

Asp Gly Asp Phe Ala Glu Leu Tyr Leu Phe Lys Trp Thr Ser Leu Leu
                 20                  25                  30

Val Pro Pro Leu Thr Leu Leu Ile Ile Asn Ile Ile Gly Val Val Val
             35                  40                  45

Gly Ile Ser Asp Ala Ile Asn Asn Gly Tyr Asp Ser Trp Gly Pro Leu
 50                  55                  60

Ile Gly Lys Leu Phe Phe Ala Phe Trp Val Ile Val His Leu Tyr Pro
 65                  70                  75                  80

Phe Leu Lys Gly Leu Met Gly Lys Gln Asp Lys Val Pro Thr Ile Ile
                 85                  90                  95

Ile Val Trp Ser Ile Leu Leu Ser Ser Ile Leu Ser Leu Leu Trp Val
                100                 105                 110

Arg Ile Asn Pro Phe Leu Asp Lys Gly Gly Ile Val Leu Glu Val Cys
            115                 120                 125

Gly Leu Asn Cys Asp Asp
        130

<210> SEQ ID NO 61
<211> LENGTH: 126
<212> TYPE: PRT
<213> ORGANISM: Cucurbita maxima

<400> SEQUENCE: 61

Gly Val Thr Ser Lys Ala Asn Asp Glu Asp Gly Asp Phe Ala Glu Leu
  1               5                  10                  15

Tyr Val Phe Lys Trp Thr Ser Leu Leu Ile Pro Pro Thr Thr Val Leu
                 20                  25                  30

Ile Met Asn Met Val Gly Ile Val Ala Gly Val Ser Tyr Ala Ile Asn
             35                  40                  45

Ser Gly Tyr Gln Ser Trp Gly Pro Leu Phe Gly Lys Leu Phe Phe Ala
 50                  55                  60

Leu Trp Val Ile Val His Leu Tyr Pro Phe Leu Lys Gly Leu Leu Gly
 65                  70                  75                  80

Arg Gln Asn Arg Thr Pro Thr Ile Val Ile Val Trp Ser Ile Leu Leu
                 85                  90                  95

Ala Ser Ile Phe Ser Leu Leu Trp Val Arg Ile Asp Pro Phe Thr Ser
                100                 105                 110

Ala Ala Thr Lys Ala Ala Asn Gly Gln Cys Gly Val Asn Cys
            115                 120                 125

<210> SEQ ID NO 62
<211> LENGTH: 139
```

```
<212> TYPE: PRT
<213> ORGANISM: Cucumis sativa

<400> SEQUENCE: 62

Asn Arg Ser Lys Gln Ile Gly Gly Gln Val Cys Gln Ile Cys Ser
  1               5                  10                  15

Asp Ser Val Gly Thr Thr Ala Asp Gly Glu Pro Phe Val Ala Cys Asp
             20                  25                  30

Val Cys Ala Phe Pro Val Cys Arg Pro Cys Tyr Glu Tyr Glu Arg Lys
         35                  40                  45

Asp Gly Asn Gln Ser Cys Pro Gln Cys Lys Thr Lys Tyr Lys Trp His
     50                  55                  60

Lys Gly Ser Pro Pro Val Thr Gly Glu Ala Val Gln Asp Gly Asp Gly
 65                  70                  75                  80

Asn Gly Val Gly Gly Ala Gln Glu Arg His His Lys Met Pro Glu Arg
                 85                  90                  95

Thr Leu Ser Trp Asp Thr Asn Tyr Asp Lys Gly Ser Phe Asn His
                100                 105                 110

Ile Pro Leu Leu Thr Thr Gly Arg Ser Val Ser Gly Glu Leu Ser Ala
            115                 120                 125

Ala Ser Pro Glu Arg Leu Ser Met Ala Ser Pro
        130                 135

<210> SEQ ID NO 63
<211> LENGTH: 196
<212> TYPE: PRT
<213> ORGANISM: Cucurbita maxima

<400> SEQUENCE: 63

Val Phe Val Ala Cys Leu Val Cys Asn Phe Pro Val Cys Arg Pro Cys
  1               5                  10                  15

Tyr Glu Tyr Glu Arg Ser Glu Gly Asn Lys Cys Cys Pro Gln Cys Asn
             20                  25                  30

Thr Arg Tyr Lys Arg His Lys Gly Ser Pro Arg Val Ile Gly Asp Asp
         35                  40                  45

Glu Glu Ala Asp Asp Ala Asp Asp Phe Asp Asp Glu Phe Pro Ile Lys
     50                  55                  60

His His Ser Asn Asp Glu Phe Glu Ser Lys Gln Pro Asn Pro Ser Glu
 65                  70                  75                  80

His Asp Asn Tyr Asn Gln Lys Asn Trp His Gln Asn Val His Ser Ser
                 85                  90                  95

Phe Ser Val Ala Gly Ser Val Asn Gly Lys Glu Met Glu Gly Glu Lys
                100                 105                 110

Glu Ser Tyr Gly Asn Ala Glu Trp Lys Glu Arg Ile Asp Lys Trp Lys
            115                 120                 125

Val Arg Gln Glu Lys Arg Gly Leu Gly Asn Lys Asp Asp Glu Ser Asn
        130                 135                 140

His Asp Gln Pro Leu Glu Asp Asp Phe Leu Leu Ala Glu Ala Arg Gln
145                 150                 155                 160

Pro Leu Trp Arg Lys Val Pro Ile Ser Ser Lys Ile Ser Pro Tyr
                165                 170                 175

Arg Ile Val Ile Val Leu Arg Leu Val Ile Leu Ala Phe Phe Arg
            180                 185                 190

Phe Arg Ile Leu
        195
```

-continued

```
<210> SEQ ID NO 64
<211> LENGTH: 86
<212> TYPE: PRT
<213> ORGANISM: Cucumis sativa

<400> SEQUENCE: 64

Ala Gly Val Ser Tyr Ala Ile Asn Ser Gly Tyr Gln Ser Trp Gly Pro
 1               5                  10                  15

Leu Phe Gly Lys Leu Phe Ala Leu Trp Val Ile Val His Leu Tyr
                20                  25                  30

Pro Phe Leu Lys Gly Leu Leu Gly Arg Gln Asn Arg Thr Pro Thr Ile
                35                  40                  45

Val Ile Val Trp Ser Ile Leu Leu Ala Ser Ile Phe Ser Leu Leu Trp
50                  55                  60

Val Arg Ile Asp Pro Phe Thr Ser Ala Ser Thr Lys Ala Ala Asn Gly
65                  70                  75                  80

Gln Cys Gly Ile Asn Cys
                85

<210> SEQ ID NO 65
<211> LENGTH: 72
<212> TYPE: PRT
<213> ORGANISM: Cucurbita maxima

<400> SEQUENCE: 65

Gly Pro Leu Phe Gly Lys Leu Phe Phe Ala Phe Trp Val Ile Ile His
 1               5                  10                  15

Leu Tyr Pro Phe Leu Lys Gly Leu Met Gly Arg Gln Asn Arg Thr Pro
                20                  25                  30

Thr Ile Val Val Trp Ser Ile Leu Leu Ala Ser Ile Phe Ser Leu
                35                  40                  45

Leu Trp Val Arg Ile Asp Pro Phe Thr Thr Arg Val Thr Gly Pro Asp
50                  55                  60

Val Glu Gln Cys Gly Ile Asn Cys
65                  70

<210> SEQ ID NO 66
<211> LENGTH: 129
<212> TYPE: PRT
<213> ORGANISM: Cucurbita maxima

<400> SEQUENCE: 66

Gly Gly Thr Gly Cys Cys Phe Asn Arg Gln Ala Leu Tyr Gly Tyr Asp
 1               5                  10                  15

Pro Val Leu Thr Glu Ala Asp Leu Glu Pro Asn Ile Ile Ile Lys Ser
                20                  25                  30

Cys Cys Gly Ser Arg Lys Lys Gly Arg Asn Lys Lys Tyr Ile Asp Lys
                35                  40                  45

Lys Arg Ala Ala Lys Arg Thr Glu Ser Thr Ile Pro Ile Phe Asn Met
                50                  55                  60

Glu Asp Ile Glu Glu Gly Val Glu Gly Tyr Asp Asp Arg Ser Leu
65                  70                  75                  80

Leu Met Ser Gln Lys Ser Leu Glu Lys Arg Phe Gly Gln Ser Pro Val
                85                  90                  95

Phe Ile Ala Ala Thr Phe Met Glu Met Gly Gly Ile Pro Pro Ser Thr
                100                 105                 110

Asn Pro Ala Thr Leu Leu Lys Glu Ser Ile His Val Ile Ser Cys Gly
```

-continued

```
              115                 120                 125
Tyr

<210> SEQ ID NO 67
<211> LENGTH: 153
<212> TYPE: PRT
<213> ORGANISM: Cucurbita maxima
<220> FEATURE:
<221> NAME/KEY: VARIANT
<222> LOCATION: (1)...(153)
<223> OTHER INFORMATION: Xaa = Any Amino Acid

<400> SEQUENCE: 67

Gly Val Ala Asn Glu Ser His Arg Xaa Thr Cys Ile Ile Asp Glu Thr
 1               5                  10                  15

Cys Arg Val Cys Gly Asp Glu Ile Gly Leu Lys Asp Asp Gly Lys Val
             20                  25                  30

Phe Val Ala Cys Leu Val Cys Asn Phe Pro Val Cys Arg Pro Cys Tyr
         35                  40                  45

Glu Tyr Glu Arg Ser Glu Gly Asn Lys Cys Cys Pro Gln Cys Asn Thr
     50                  55                  60

Arg Tyr Lys Arg His Lys Gly Ser Pro Arg Val Ile Gly Asp Asp Glu
 65                  70                  75                  80

Glu Val Asp Asp Ala Asp Asp Phe Asp Asp Glu Phe Pro Ile Lys His
                 85                  90                  95

His Ser Asn Asp Glu Phe Glu Ser Lys Gln Pro Asn Pro Ser Glu His
            100                 105                 110

Asp Asn Tyr Asn Gln Lys Asn Trp His Gln Asn Val His Ser Ser Phe
        115                 120                 125

Ser Val Ala Gly Ser Val Asn Gly Lys Glu Met Glu Gly Glu Lys Lys
    130                 135                 140

Lys Lys Lys Lys Lys Lys Pro Cys
145                 150

<210> SEQ ID NO 68
<211> LENGTH: 42
<212> TYPE: PRT
<213> ORGANISM: Cucurbita maxima

<400> SEQUENCE: 68

Thr Pro Thr Ile Val Val Trp Ser Ile Leu Leu Ala Ser Ile Phe
 1               5                  10                  15

Ser Leu Leu Trp Val Arg Ile Asp Pro Phe Thr Arg Val Thr Gly
             20                  25                  30

Pro Asp Val Glu Gln Cys Gly Ile Asn Cys
         35                  40

<210> SEQ ID NO 69
<211> LENGTH: 152
<212> TYPE: PRT
<213> ORGANISM: Cucurbita maxima

<400> SEQUENCE: 69

Met Ala Phe Ala Gly Thr Thr Gln Lys Cys Met Ala Cys Asp Lys Thr
 1               5                  10                  15

Val Tyr Leu Val Asp Lys Leu Thr Ala Asp Asn Arg Val Tyr His Lys
             20                  25                  30

Ala Cys Phe Arg Cys His His Cys Lys Gly Thr Leu Lys Leu Ser Asn
         35                  40                  45
```

```
Tyr Asn Ser Phe Glu Gly Val Leu Tyr Cys Arg Pro His Phe Asp Gln
         50                  55                  60

Leu Phe Lys Arg Thr Gly Ser Leu Asp Lys Ser Phe Glu Gly Thr Pro
 65                  70                  75                  80

Lys Ile Gly Lys Pro Glu Lys Pro Ala Asp Ser Glu Arg Pro Thr Ala
                 85                  90                  95

Thr Lys Val Ala Ser Met Phe Val Gly Thr Lys Asp Lys Cys Leu Gly
            100                 105                 110

Cys Lys Asn Thr Val Tyr Pro Thr Glu Lys Val Ser Val Asn Gly Thr
            115                 120                 125

Ser Tyr His Lys Ser Cys Phe Lys Cys Cys His Gly Arg Cys Thr Ile
        130                 135                 140

Ser Pro Ser Asn Tyr Ile Ala His
145                 150
```

<210> SEQ ID NO 70
<211> LENGTH: 189
<212> TYPE: PRT
<213> ORGANISM: Cucumis sativa

<400> SEQUENCE: 70

```
Met Ser Phe Ile Gly Thr Gln Gln Lys Cys Lys Ala Cys Glu Lys Thr
  1               5                  10                  15

Val Tyr Pro Val Glu Gln Leu Ser Ala Asp Gly Val Ser Tyr His Lys
             20                  25                  30

Ser Cys Phe Lys Cys Ser His Cys Lys Gly Thr Leu Lys Leu Ser Asn
         35                  40                  45

Tyr Ser Ser Met Glu Gly Val Leu Tyr Cys Lys Pro His Phe Glu Gln
     50                  55                  60

Leu Phe Lys Glu Thr Gly Asn Phe Asn Lys Asn Phe Gln Ser Pro Ala
 65                  70                  75                  80

Lys Ser Ala Glu Lys Leu Thr Pro Glu Leu Thr Arg Ser Pro Ser Lys
                 85                  90                  95

Ala Ala Gly Met Phe Ser Gly Thr Gln Asp Lys Cys Ala Thr Cys Gly
            100                 105                 110

Lys Thr Val Tyr Pro Leu Glu Lys Val Thr Val Glu Ser Gln Ser Tyr
            115                 120                 125

His Lys Ser Cys Phe Lys Cys Ser His Gly Gly Cys Ala Leu Ser Pro
        130                 135                 140

Ser Asn Tyr Ala Ala Leu Glu Gly Ile Leu Tyr Cys Lys His His Phe
145                 150                 155                 160

Ser Gln Leu Phe Lys Glu Lys Gly Ser Tyr Asn His Leu Ile Lys Cys
                165                 170                 175

Ala Ser Met Lys Arg Ser Ala Ala Pro Val Pro Glu Ala
            180                 185
```

<210> SEQ ID NO 71
<211> LENGTH: 184
<212> TYPE: PRT
<213> ORGANISM: Cucurbita maxima

<400> SEQUENCE: 71

```
Met Ala Phe Leu Gly Thr Thr Gln Lys Cys Lys Ala Cys Asp Lys Thr
  1               5                  10                  15

Val Tyr Leu Val Asp Gln Leu Thr Ala Asp Asn Lys Ile Tyr His Lys
             20                  25                  30
```

```
Ala Cys Phe Arg Cys Tyr His Cys Lys Ser Thr Leu Lys Leu Phe Asn
             35                  40                  45
Tyr Ser Ser Phe Glu Gly Val Leu Tyr Cys Lys Pro His Phe Asp Gln
 50                  55                  60
Leu Phe Lys Met Thr Gly Ser Leu Glu Lys Ser Phe Glu Gly Thr Pro
 65                  70                  75                  80
Arg Thr Ile Arg Thr Asp Arg Ser Thr Asn Gln Val Gln Ser Asn Ser
             85                  90                  95
Lys Val Ser Ser Leu Phe Ala Gly Thr Gln Asp Lys Cys Val Thr Cys
            100                 105                 110
Lys Lys Thr Val Tyr Pro Ile Glu Lys Val Ala Val Asp Ser Lys Ser
            115                 120                 125
Tyr His Arg Ala Cys Phe Arg Cys Ser His Gly Gly Cys Val Ile Ser
            130                 135                 140
Pro Ser Asn Tyr Ile Ala His Glu His Arg Leu Tyr Cys Arg His His
145                 150                 155                 160
His Asn Gln Leu Phe Lys Gln Lys Gly Asn Phe Ser Gln Leu Asp Lys
            165                 170                 175
His Glu Glu Ile Lys Gly Ser Asp
            180
```

```
<210> SEQ ID NO 72
<211> LENGTH: 122
<212> TYPE: PRT
<213> ORGANISM: Cucurbita maxima

<400> SEQUENCE: 72

Met Ser Phe Thr Gly Thr Gln Gln Lys Cys Lys Ala Cys Glu Lys Thr
 1                   5                  10                  15
Val Tyr Pro Val Glu Gln Leu Ser Ala Asp Gly Val Ser Tyr His Lys
             20                  25                  30
Ser Cys Phe Lys Cys Ser His Cys Lys Gly Thr Leu Lys Leu Ser Asn
             35                  40                  45
Tyr Cys Ser Met Glu Gly Val Leu Tyr Cys Lys Pro His Phe Glu Gln
 50                  55                  60
Leu Phe Lys Glu Thr Gly Asn Phe Asn Lys Asn Phe Gln Ser Pro Ala
 65                  70                  75                  80
Lys Ser Ala Glu Lys Thr Pro Glu Leu Thr Arg Ser Pro Ser Lys Ala
             85                  90                  95
Ala Gly Met Phe Ser Gly Thr Gln Asp Lys Cys Ala Thr Cys Gly Lys
            100                 105                 110
Thr Val Tyr Pro Leu Glu Lys Val Ser Thr
            115                 120
```

```
<210> SEQ ID NO 73
<211> LENGTH: 178
<212> TYPE: PRT
<213> ORGANISM: Cucumis sativa

<400> SEQUENCE: 73

Cys Lys Ala Cys Asp Lys Thr Val Tyr Pro Val Asp Gln Leu Ser Ala
 1                   5                  10                  15
Asp Gly Val Ser Phe His Lys Ser Cys Phe Lys Cys Ser His Cys Lys
             20                  25                  30
Gly Thr Leu Lys Leu Ser Asn Tyr Ser Ser Met Asp Gly Val Leu Tyr
             35                  40                  45
```

```
Cys Lys Pro His Phe Glu Gln Leu Phe Lys Glu Thr Gly Asn Phe Ser
     50                  55                  60

Lys Asn Phe Leu Ser Pro Ala Lys Ser Ser Glu Lys Leu Thr Pro Glu
 65                  70                  75                  80

Leu Thr Arg Ser Pro Ser Lys Ala Ala Ser Met Phe Ser Gly Thr Gln
                 85                  90                  95

Glu Lys Cys Ala Thr Cys Gly Lys Thr Ala Tyr Pro Leu Glu Lys Val
            100                 105                 110

Thr Val Glu Ser Gln Ala Tyr His Lys Ser Cys Phe Lys Cys Ser His
            115                 120                 125

Gly Gly Cys Ser Leu Ser Pro Ser Asn Tyr Ala Ala Leu Asp Gly Ile
        130                 135                 140

Leu Tyr Cys Lys His His Phe Ser Gln Leu Phe Lys Glu Lys Gly Ser
145                 150                 155                 160

Tyr Asn His Leu Ile Lys Ser Ala Ser Met Lys Arg Gln Ala Ala Thr
                165                 170                 175

Ser Asp

<210> SEQ ID NO 74
<211> LENGTH: 126
<212> TYPE: PRT
<213> ORGANISM: Cucurbita maxima

<400> SEQUENCE: 74

Ser Ile Phe Asp Asp Gly Gln Gln His Gln His Phe Ala Tyr Thr Val
  1               5                  10                  15

Gln Leu Val Thr Ser Ala Asp Val Pro Met Thr Leu Gln Ala Pro Ser
             20                  25                  30

Ser Ser Ala Cys Val Arg Ser Trp Pro Arg Pro Ala Met Gly Pro Ser
             35                  40                  45

Cys Leu Arg Leu Arg Ile Thr Ala Lys Ile Thr Thr Ser Asn Tyr Asp
     50                  55                  60

Ala Ala Ser Met Ile Asp Arg Ile Leu Thr Leu Met Ala Ala His Ser
 65                  70                  75                  80

Val Val Gly Cys Ser Val Ile Ile Asp Glu Asn Gly Asn Lys Gln Arg
                 85                  90                  95

Leu Tyr Ser Leu Thr Pro Val Ala Lys Tyr Leu Val Leu Asp Glu Asp
            100                 105                 110

Gly Val Ser Leu Gly Val Leu Leu Ser Met Ile Gln Asp Lys
            115                 120                 125

<210> SEQ ID NO 75
<211> LENGTH: 161
<212> TYPE: PRT
<213> ORGANISM: Cucurbita maxima

<400> SEQUENCE: 75

Met Ile Ser Val Pro Met Ser Leu Asn Ala Val Val Arg Leu Lys Ile
  1               5                  10                  15

Ala Asp Ala Ile Trp Gln Gly Gly Ser Asn Phe Pro Leu Ser Ala Ser
             20                  25                  30

Glu Ile Leu Ala Arg Leu Val Pro Ser Gly Gly Asp Ala Asp Asn Leu
             35                  40                  45

Glu Arg Ile Leu Arg Met Leu Thr Ser Tyr Gly Val Phe Glu Glu His
     50                  55                  60
```

```
Leu Asn Pro Asn Ser Ser Asp Arg Arg Tyr Ser Leu Thr Asp Val Gly
 65                  70                  75                  80

Lys Thr Leu Val Thr Asp Ser Asp Gly Leu Ser Tyr Ala Ser Tyr Val
                 85                  90                  95

Leu Gln His His Gln Asp Ala Leu Met Arg Ala Trp Pro Arg Val His
            100                 105                 110

Glu Ala Ala Ile Asp Ala Thr Thr Glu Pro Phe Val Arg Ala Asn Gly
            115                 120                 125

Glu Ala Ala Tyr Ser Tyr Tyr Gly Lys Asn Glu Glu Met Asn Leu Leu
            130                 135                 140

Met Gln Arg Ala Met Ala Gly Val Ser Val Pro Phe Met Lys Ala Val
145                 150                 155                 160

Leu

<210> SEQ ID NO 76
<211> LENGTH: 198
<212> TYPE: PRT
<213> ORGANISM: Cucumis sativa

<400> SEQUENCE: 76

Met Glu Gln His Asn Thr Ser Thr Thr Ala Asp Ser Glu Ile Gln Asn
  1               5                  10                  15

Lys Ala Arg Leu Ala Ile Ile Glu Leu Ala Asn Met Ile Ser Val Pro
                 20                  25                  30

Met Ser Leu Asn Ala Ile Val Arg Leu Asn Val Ala Asp Ala Ile Trp
             35                  40                  45

Gln Asn Gly Ser Asn Ser Pro Leu Ser Ala Ser Glu Ile Leu Ala Arg
         50                  55                  60

Val Val Pro Ser Gly Gly Asp Ala His Asn Leu Glu Arg Ile Leu Arg
 65                  70                  75                  80

Met Leu Thr Ser Tyr Gly Val Phe Glu Glu His Leu Ser Pro Asn Ser
                 85                  90                  95

Ser Asn His Arg Tyr Ser Leu Thr Asp Val Gly Lys Thr Leu Val Thr
            100                 105                 110

Asp Ser Asp Gly Leu Ser Tyr Ala Pro Tyr Val Leu Gln His His Gln
            115                 120                 125

Asp Ala Leu Met Arg Ala Trp Pro Arg Val His Glu Ala Ala Ile Asp
            130                 135                 140

Ser Thr Thr Glu Pro Phe Val Arg Ala Asn Gly Glu Ala Ala Tyr Ser
145                 150                 155                 160

Tyr Tyr Gly Lys Lys Thr Glu Met Asn Glu Leu Met Gln Arg Ala Met
                165                 170                 175

Ala Gly Val Ser Val Pro Phe Met Lys Ala Val Leu Asp Gly Tyr Asp
            180                 185                 190

Gly Phe Lys Gly Val Glu
        195

<210> SEQ ID NO 77
<211> LENGTH: 316
<212> TYPE: PRT
<213> ORGANISM: Cucumis sativa

<400> SEQUENCE: 77

Met Ser Leu Gly Val Ser Asn Asp Glu Glu Glu Ala Gln Leu Phe Ala
  1               5                  10                  15

Met Gln Leu Ala Ser Ala Ser Val Leu Pro Met Val Leu Lys Thr Ala
```

```
                      20                  25                  30
Ile Glu Leu Asp Leu Leu Glu Ile Ile Gly Arg Gly Gly Glu Gly Ala
            35                  40                  45

Leu Leu Ser Pro Ser Gln Ile Ala Ser Gln Leu Ser Gly Leu Lys Asn
    50                  55                  60

Pro Glu Ala His Val Met Leu Asp Arg Met Leu Arg Leu Leu Ala Ser
65                  70                  75                  80

Tyr Ser Ile Leu Thr Cys Ser Leu Asp Pro Leu Pro Asp Gly Ser Val
                85                  90                  95

Gln Arg Leu Tyr Gly Leu Ala Pro Val Ser Lys Phe Leu Ile Lys Asn
            100                 105                 110

His Asp Gly Val Ser Ile Ala Pro Leu Cys Leu Met Asn Gln Asp Lys
        115                 120                 125

Val Leu Met Glu Ser Trp Tyr His Leu Lys Asp Ala Val Leu Glu Gly
    130                 135                 140

Gly Ile Pro Phe Asn Arg Ala Tyr Gly Met Ser Ala Phe Glu Tyr His
145                 150                 155                 160

Gly Thr Asp Pro Arg Phe Asn Lys Val Phe Asn Lys Gly Met Ser Asp
                165                 170                 175

His Ser Thr Ile Thr Met Lys Lys Ile Leu Glu Thr Tyr Lys Gly Phe
            180                 185                 190

Glu Gly Leu Asn Ser Val Val Asp Val Gly Gly Thr Gly Ala Val
        195                 200                 205

Leu Asn Met Ile Val Ser Lys Tyr Pro Ser Ile Arg Gly Ile Asn Phe
    210                 215                 220

Asp Leu Pro His Val Ile Gln Asp Ala Pro Pro Tyr Pro Gly Val Glu
225                 230                 235                 240

His Val Gly Gly Asp Met Phe Val Ser Val Pro Lys Gly Asp Ala Ile
                245                 250                 255

Phe Met Lys Trp Ile Cys His Asp Trp Ser Asp His His Cys Leu Lys
            260                 265                 270

Phe Leu Lys Asn Cys Tyr Asp Ala Leu Pro Glu His Gly Lys Val Ile
        275                 280                 285

Val Ala Glu Cys Ile Leu Pro Leu Ala Pro Asp Ala Ser Leu Ala Thr
    290                 295                 300

Lys Gly Val Ile His Ile Asp Leu Ile Met Leu Ala
305                 310                 315

<210> SEQ ID NO 78
<211> LENGTH: 361
<212> TYPE: PRT
<213> ORGANISM: Cucumis sativa

<400> SEQUENCE: 78

Met Ala Ser Ser Asp Asn Asp Thr Ala Val Glu Gln Gln Gln His Tyr
 1               5                  10                  15

Ala Tyr Ala Gly His Leu Val Thr Leu Ser Val Leu Pro Met Thr Leu
            20                  25                  30

Gln Ala Val Phe Glu Leu Gly Val Phe Glu Ile Leu Ala Lys Ala Gly
        35                  40                  45

Asp Gly Ala Asn Leu Ser Pro Ala Glu Ile Ala Ala Glu Ile Thr Thr
    50                  55                  60

Thr Asn Pro Asn Ala Ala Leu Met Leu Asp Arg Met Leu Arg Leu Leu
65                  70                  75                  80
```

```
Ala Cys His Ser Val Gly Cys Ser Ile Val Ser Asp Lys Asp Gly
            85                  90                  95

Asn Val Gln Arg Leu Tyr Ser Leu Thr Pro Ile Ser Lys Cys Tyr Val
            100                 105                 110

Arg Asn Glu Asp Gly Val Ser Leu Gly Pro Met Leu Ser Leu Ile Gln
            115                 120                 125

Asp Lys Val Phe Leu Gln Ser Trp Ser Glu Leu Lys Asn Ala Val Thr
130                 135                 140

Glu Gly Gly Val Pro Phe Asp Arg Ala His Gly Gly Val Asn Ala Phe
145                 150                 155                 160

Glu Tyr Pro Lys Leu Asp Pro Arg Phe Asn Gln Val Phe Asn Ile Ala
            165                 170                 175

Met Val Asn His Thr Thr Met Ser Ile Lys Lys Ile Val Glu Ser Tyr
            180                 185                 190

Lys Gly Phe Ala Asn Ile Lys Gln Leu Val Asp Val Gly Gly Gly Leu
            195                 200                 205

Gly Val Thr Leu Gln Ile Ile Thr Ser Thr Tyr Pro Ser Ile Lys Gly
            210                 215                 220

Ile Asn Phe Asp Leu Pro His Val Ile Arg Asp Ala Pro Ala Tyr Asn
225                 230                 235                 240

Gly Val Gln His Val Gly Gly Asp Met Phe Glu Ser Val Pro Asn Gly
            245                 250                 255

Asp Ala Ile Phe Met Lys Trp Ile Leu His Asp Trp Ser Asp Asp His
            260                 265                 270

Cys Thr Lys Leu Leu Lys Asn Cys Tyr Asn Ala Ile Pro Asp Asp Gly
            275                 280                 285

Lys Ile Ile Ile Val Glu Ser Val Ile Pro Thr Lys Pro Glu Ile Thr
290                 295                 300

Asn Val Thr Lys Ala Thr Thr Gln Gly Asp Val Leu Met Met Thr Gln
305                 310                 315                 320

Asn Pro Gly Gly Lys Glu Arg Thr Arg Asp Glu Phe Lys Ser Leu Ala
            325                 330                 335

Thr Lys Ala Gly Phe Lys His Val Met Phe Glu Cys Phe Val Ala Asn
            340                 345                 350

Leu Trp Val Ile Glu Leu Leu Lys Asn
            355                 360

<210> SEQ ID NO 79
<211> LENGTH: 214
<212> TYPE: PRT
<213> ORGANISM: Cucurbita maxima

<400> SEQUENCE: 79

Met Gly Ser Ser Gly Lys Gly Cys Glu Val Gln Ile Thr Pro Thr Thr
1               5                   10                  15

Arg Val Ser Asp Glu Glu Ala Gln Leu Phe Ala Met Gln Leu Ala Ser
            20                  25                  30

Ala Ser Val Leu Pro Met Val Leu Lys Ala Ala Ile Glu Leu Asp Val
            35                  40                  45

Leu Glu Ile Ile Gly Ala Ala Gly Glu Gly Ala Leu Leu Ser Pro Ser
            50                  55                  60

Gln Ile Ala Ser His Leu Ser Tyr Ser Ile Leu Thr Tyr Ser Leu Asn
65                  70                  75                  80

Thr Leu Pro Asp Gly Ser Leu Gln Arg Leu Tyr Gly Leu Ala Pro Val
            85                  90                  95
```

```
Ala Lys Phe Leu Val Lys Asn Gln Asp Gly Val Ser Ile Ala Pro Leu
            100                 105                 110

Cys Leu Met Asn Gln Asp Lys Val Leu Met Glu Ser Trp Tyr His Leu
            115                 120                 125

Lys Asp Ala Val Leu Glu Gly Gly Ile Pro Phe Asn Lys Ala Tyr Gly
            130                 135                 140

Met Thr Ala Phe Glu Tyr His Gly Thr Asp Pro Arg Phe Asn Arg Val
145                 150                 155                 160

Phe Asn Arg Gly Met Ser Asp His Ser Thr Ile Thr Met Lys Lys Ile
                165                 170                 175

Leu Glu Thr Tyr Lys Gly Phe Glu Gly Leu Asn Ser Leu Val Asp Val
            180                 185                 190

Gly Gly Gly Thr Gly Ala Val Leu Asn Met Ile Val Ser Lys Tyr Pro
            195                 200                 205

Ser Ile Arg Gly Ile Asn
            210

<210> SEQ ID NO 80
<211> LENGTH: 286
<212> TYPE: PRT
<213> ORGANISM: Cucurbita maxima

<400> SEQUENCE: 80

Met Gly Ser Ser Gly Lys Gly Cys Glu Val Gln Ile Thr Pro Thr Thr
 1               5                  10                  15

Arg Val Ser Asp Glu Glu Ala Gln Leu Phe Ala Met Gln Leu Ala Ser
            20                  25                  30

Ala Ser Val Leu Pro Met Val Leu Lys Ala Ala Ile Glu Leu Asp Val
            35                  40                  45

Leu Glu Ile Ile Gly Ala Ala Gly Glu Gly Ala Leu Leu Ser Pro Ser
        50                  55                  60

Gln Ile Ala Ser His Leu Ser Phe Ser Gly Ala Lys Thr Pro Asn Pro
65                  70                  75                  80

Glu Ala Gly Val Val Leu Asp Arg Met Leu Arg Leu Leu Ala Ser Tyr
                85                  90                  95

Ser Ile Leu Thr Tyr Ser Leu Asn Thr Leu Pro Asp Gly Ser Leu Gln
            100                 105                 110

Arg Leu Tyr Gly Leu Ala Pro Val Ala Lys Phe Leu Val Lys Asn Gln
            115                 120                 125

Asp Gly Val Ser Ile Ala Pro Leu Cys Leu Met Asn Gln Asp Lys Val
            130                 135                 140

Leu Met Glu Ser Trp Tyr His Leu Lys Asp Ala Val Leu Glu Gly Gly
145                 150                 155                 160

Ile Pro Phe Asn Lys Ala Tyr Gly Met Thr Ala Phe Glu Tyr His Gly
                165                 170                 175

Thr Asp Pro Arg Phe Asn Arg Val Phe Asn Arg Gly Met Ser Asp His
            180                 185                 190

Ser Thr Ile Thr Met Lys Lys Ile Leu Glu Thr Tyr Lys Gly Phe Glu
            195                 200                 205

Gly Leu Asn Ser Val Val Asp Val Gly Gly Gly Thr Gly Ala Val Leu
            210                 215                 220

Asn Met Ile Val Ser Lys Tyr Pro Ser Ile Arg Gly Ile Asn Phe Asp
225                 230                 235                 240

Leu Pro His Val Ile Gln Asp Ala Pro Ala Tyr Pro Gly Val Gln His
```

-continued

```
                245                 250                 255
Val Gly Gly Asp Met Phe Val Ser Val Pro Lys Gly Asp Ala Ile Phe
            260                 265                 270

Met Lys Trp Ile Cys His Asp Trp Ser Asp Gln His Cys Leu
            275                 280                 285

<210> SEQ ID NO 81
<211> LENGTH: 195
<212> TYPE: PRT
<213> ORGANISM: Cucurbita maxima

<400> SEQUENCE: 81

Arg Lys Gln Arg Ser Cys Leu Lys Ala Lys Gln Arg Tyr Trp Lys Tyr
  1               5                  10                  15

Met Leu Cys Phe Ala Asp Ser Met Ala Leu Lys Cys Ala Val Glu Leu
                 20                  25                  30

His Leu Ala Asp Ile Ile Asn Ser His Ala Ser Pro Leu Ser Leu Ser
             35                  40                  45

Gln Ile Ala Ser Ser Ile Val Ala Ser Asp Pro Leu Ala Thr Pro Glu
     50                  55                  60

Ile Ser Tyr Leu Thr Arg Ile Met Arg Leu Leu Val Arg Arg Asn Ile
 65                  70                  75                  80

Phe Ala Val His His Ser Pro Asp Gly Gly Glu Pro Leu Tyr Gly Leu
                 85                  90                  95

Thr His Ser Ser Lys Trp Leu Leu Arg Asp Ala Glu His Thr Leu Ala
                100                 105                 110

Pro Met Val Leu Ala Glu Leu His Lys Trp Met Val Asp Pro Trp Leu
            115                 120                 125

Cys Phe Ser Gln Gly Val Lys Glu Gly Gly Asp Gln Phe Gln Lys Ala
        130                 135                 140

Asn Gly Leu Asp Ile Trp Ser Phe Ala Ser Arg Asn Pro Gln Phe Asn
145                 150                 155                 160

Gln Leu Phe Ile Asn Ala Met Ala Ser Thr Ser Lys Val Ile Met Lys
                165                 170                 175

Ala Val Leu Ser Val Tyr Gln Asp Gly Phe Ser Ser Ile Glu Ser Leu
            180                 185                 190

Thr Asp Val
        195

<210> SEQ ID NO 82
<211> LENGTH: 327
<212> TYPE: PRT
<213> ORGANISM: Cucurbita maxima

<400> SEQUENCE: 82

Met Ala Val Tyr Gly Gly Asp Val Pro Gln Val Asp Pro Arg Ser Gly
  1               5                  10                  15

Phe Cys Lys Ser Thr Lys Ile Phe His Ser Lys Arg Arg Pro Ile Pro
                 20                  25                  30

Leu Pro Pro Asn Gln Ser Leu Asp Ala Thr Thr Phe Ile Ser Ser Arg
             35                  40                  45

Pro His Asn Gly Lys Ile Ala Leu Ile Asp Ala Thr Thr Gly Gln His
     50                  55                  60

Ile Thr Tyr Ser His Leu Trp Glu Ser Val Asp Ser Val Ala Ser Phe
 65                  70                  75                  80

Leu Ser Asp Met Gly Ile Arg Lys Gly His Val Ile Leu Leu Leu Ser
```

-continued

```
                85                  90                  95
Pro Asn Ser Ile Phe Phe Pro Ile Ile Cys Leu Ala Val Met Ser Leu
            100                 105                 110
Gly Ala Val Ile Thr Thr Thr Asn Pro Leu Asn Thr Pro Gln Glu Ile
            115                 120                 125
Ala Lys Gln Ile Ala Asp Ser Asn Pro Ile Leu Ala Phe Thr Thr Gln
        130                 135                 140
Gln Leu Ile Pro Lys Ile Ala Ser Ser Lys Leu Pro Val Val Leu Ile
145                 150                 155                 160
Asp Gly Glu Ile Gln Ile Lys Lys Phe Ser Val Lys Ile Val Ser Thr
                165                 170                 175
Leu Ser Glu Met Met Arg Lys Lys Ser Ser Gly Ser Arg Val Lys Glu
            180                 185                 190
Arg Val Asp Gln Asn Asp Thr Ala Thr Leu Leu Tyr Ser Ser Gly Thr
            195                 200                 205
Thr Gly Ala Ser Lys Gly Val Val Ser Ser His Lys Asn Leu Ile Ala
        210                 215                 220
Met Val Gln Val Val Thr Arg Phe Lys Leu Ser Glu Gly Glu Gly
225                 230                 235                 240
Thr Phe Ile Cys Thr Val Pro Met Phe His Ile Tyr Gly Leu Val Ala
                245                 250                 255
Phe Ala Thr Gly Leu Leu Ser Ser Gly Ser Thr Ile Val Val Leu Ser
            260                 265                 270
Lys Phe Glu Ile His Glu Met Leu Ser Ala Ile Glu Lys Tyr Arg Ala
            275                 280                 285
Thr Tyr Leu Pro Leu Val Pro Pro Ile Leu Val Ala Met Val Asn Ala
        290                 295                 300
Ala Glu Gln Ile Lys Gly Lys Tyr Asp Leu Gly Ser Leu His Thr Ala
305                 310                 315                 320
Leu Ser Gly Gly Ala Pro Leu
                325
```

<210> SEQ ID NO 83
<211> LENGTH: 212
<212> TYPE: PRT
<213> ORGANISM: Cucurbita maxima

<400> SEQUENCE: 83

```
Met Ala Asn Glu Thr Val His Asp Phe Ile Phe Arg Ser Lys Leu Pro
  1               5                  10                  15
Asp Ile Tyr Ile Pro Lys His Leu Pro Leu His Ser Tyr Cys Leu Gln
                20                  25                  30
Glu Lys Met Ala Glu Ile Gly His Arg Thr Cys Leu Ile Asn Ala Val
            35                  40                  45
Thr Gly Glu Ser Phe Thr Tyr Ser Asp Val Asp Leu Ala Ala Arg Lys
        50                  55                  60
Ala Ala Ser Gly Leu Tyr Lys Leu Gly Ile Ala Lys Gly Asp Val Ile
 65                  70                  75                  80
Met Leu Leu Leu Pro Asn Ser Pro Glu Phe Val Phe Ala Phe Leu Gly
                85                  90                  95
Ala Ser Tyr Leu Gly Ala Ile Met Thr Ala Ala Asn Pro Phe Phe Thr
            100                 105                 110
Ala Ala Glu Ile Ala Lys Gln Ala Lys Gly Ser Lys Ala Lys Leu Thr
            115                 120                 125
```

```
Ile Thr Gln Ser Ser Tyr Tyr Glu Lys Val Lys Glu Ile Thr Glu Gln
        130                 135                 140

Leu Pro Asp Ala Lys Ile Met Thr Ile Asp Ser Pro Leu Gly Cys
145                 150                 155                 160

Leu Ser Phe Ala Asp Leu Ile Gln Gly Gly Asp His Glu Ile Pro Ala
                    165                 170                 175

Val Glu Ile Ser Pro Asp Asp Val Val Ala Leu Pro Tyr Ser Ser Gly
                180                 185                 190

Thr Thr Gly Leu Pro Lys Gly Val Met Leu Thr His Lys Gly Leu Val
            195                 200                 205

Thr Ser Val Ala
    210
```

<210> SEQ ID NO 84
<211> LENGTH: 194
<212> TYPE: PRT
<213> ORGANISM: Cucurbita maxima

<400> SEQUENCE: 84

```
Met Ala Val Glu Ala Leu Gln Asn Asp Phe Ile Phe Arg Ser Lys Leu
1               5                   10                  15

Pro Asp Ile Tyr Ile Pro Asn His Leu Pro Leu His Ser Tyr Cys Leu
                20                  25                  30

His Glu Asn Leu Ala Lys Ile Gly His Arg Thr Cys Leu Ile Asn Ala
            35                  40                  45

Val Thr Ala Glu Ser Phe Thr Tyr His Asp Val Asp Leu Ala Ala Arg
    50                  55                  60

Lys Val Ala Ser Gly Leu Asn Lys Leu Gly Ile Ala Gln Gly Asp Val
65                  70                  75                  80

Ile Leu Leu Leu Leu Gln Asn Ser Pro Glu Phe Val Phe Ala Phe Leu
                85                  90                  95

Gly Ala Ser Tyr Arg Gly Ala Ile Met Thr Ala Ala Asn Pro Phe Phe
                100                 105                 110

Thr Ala Ala Glu Ile Ala Lys Gln Ala Lys Gly Ser Asn Ala Lys Leu
            115                 120                 125

Ile Val Thr Gln Ser Ser Tyr Tyr Glu Lys Val Lys Glu Ile Thr Glu
    130                 135                 140

Glu Leu Pro Asp Val Lys Ile Met Thr Val Asp Ser Pro Pro Asp Gly
145                 150                 155                 160

Cys Leu Ser Phe Ala Asp Leu Ile Gln Ala Asp Glu Arg Glu Met Pro
                165                 170                 175

Thr Val Glu Ile Asn Pro Asp Asp Val Val Ala Leu Pro Tyr Ser Ser
                180                 185                 190

Gly Thr
```

<210> SEQ ID NO 85
<211> LENGTH: 153
<212> TYPE: PRT
<213> ORGANISM: Cucurbita maxima

<400> SEQUENCE: 85

```
Gln Asn Asp Thr Ala Thr Leu Tyr Ser Ser Gly Thr Thr Gly Ala
1               5                   10                  15

Ser Lys Gly Val Val Ser Ser His Lys Asn Leu Ile Ala Met Val Gln
                20                  25                  30

Val Val Val Thr Arg Phe Arg Leu Ser Glu Gly Glu Gly Thr Phe Ile
```

```
                35                  40                  45
Cys Thr Val Pro Met Phe His Ile Tyr Gly Leu Val Ala Phe Ala Thr
     50                  55                  60
Gly Leu Leu Ser Ser Gly Ser Thr Ile Ile Val Leu Ser Lys Phe Glu
 65                  70                  75                  80
Ile His Glu Met Leu Ser Ala Ile Glu Lys Tyr Arg Ala Thr Tyr Leu
                 85                  90                  95
Pro Leu Val Pro Pro Ile Leu Val Ala Leu Val Asn Ala Ala Glu Gln
                100                 105                 110
Ile Lys Gly Lys Tyr Asp Leu Ser Ser Leu His Thr Ala Leu Ser Gly
                115                 120                 125
Gly Ala Pro Leu Gly Lys Glu Val Ile Glu Gly Phe Val Glu Lys Tyr
            130                 135                 140
Pro Asn Arg Arg Ser Val Leu His Arg
145                 150

<210> SEQ ID NO 86
<211> LENGTH: 143
<212> TYPE: PRT
<213> ORGANISM: Cucurbita maxima

<400> SEQUENCE: 86

Thr Ile Arg Ser Asp Ser Arg His Asn Arg Gln Gly Trp Gly Leu His
  1               5                  10                  15
Thr Gly Asp Ile Gly Phe Ile Asp Asp Asp Glu Leu Phe Ile Val
                 20                  25                  30
Asp Arg Leu Lys Glu Leu Ile Lys Tyr Lys Gly Phe Gln Val Ala Pro
             35                  40                  45
Ala Glu Leu Glu Ala Leu Leu Thr His Pro Ala Ile Ser Asp Ala
         50                  55                  60
Ala Val Val Pro Met Lys Asp Glu Ala Gly Glu Val Pro Val Ala
 65                  70                  75                  80
Phe Val Val Arg Leu Lys Asn Ser Glu Val Thr Glu Asp Glu Ile Lys
                 85                  90                  95
Gln Phe Ile Ser Lys Gln Val Val Phe Tyr Lys Arg Ile Lys Arg Ala
                100                 105                 110
Phe Met Ile Asp Ala Ile Pro Lys Ser Pro Ser Gly Lys Ile Leu Arg
             115                 120                 125
Lys Glu Leu Arg Ala Lys Leu Ala Thr Gly Phe Pro Ile Ser Asn
        130                 135                 140

<210> SEQ ID NO 87
<211> LENGTH: 195
<212> TYPE: PRT
<213> ORGANISM: Cucumis sativa

<400> SEQUENCE: 87

Ala Pro Pro Asp Gly Cys Leu Trp Phe Gly Asp Leu Ile Lys Ala Asp
  1               5                  10                  15
Glu Arg Glu Val Pro Arg Val Asp Ile Asp Pro Glu Asp Val Val Ala
                 20                  25                  30
Leu Pro Tyr Ser Ser Gly Thr Thr Gly Leu Pro Lys Gly Val Met Leu
             35                  40                  45
Thr His Lys Ser Leu Val Thr Ser Val Ala Gln Gln Val Asp Gly Glu
         50                  55                  60
Asn Pro Asn Leu Tyr Tyr Gly His Glu Asp Val Ile Leu Cys Val Leu
```

```
                65                  70                  75                  80
Pro Leu Phe His Ile Tyr Ser Leu Asn Ser Val Leu Leu Cys Gly Leu
                        85                  90                  95
Arg Ala Gly Ser Thr Ile Leu Ile Met Pro Lys Phe Glu Ile Gly Leu
                100                 105                 110
Leu Leu Gln Leu Ala Glu Lys Tyr Gly Val Thr Val Ala Pro Ile Val
                115                 120                 125
Pro Pro Ile Val Leu Ala Ile Ala Lys Ser Pro Glu Leu Glu Lys Tyr
        130                 135                 140
Asp Leu Ser Ser Ile Arg Ile Ile Lys Ser Gly Gly Ala Pro Leu Gly
145                 150                 155                 160
Lys Glu Leu Glu Asp Thr Val Arg Ala Lys Phe Pro Lys Ala Val Leu
                165                 170                 175
Gly Gln Gly Tyr Gly Met Thr Glu Ala Gly Pro Val Pro Thr Met Gly
                180                 185                 190
Leu Ala Phe
        195

<210> SEQ ID NO 88
<211> LENGTH: 124
<212> TYPE: PRT
<213> ORGANISM: Cucurbita maxima

<400> SEQUENCE: 88

Asp Leu Ser Ser Ile Arg Met Ile Lys Ser Gly Gly Ala Pro Leu Gly
1               5                   10                  15
Lys Glu Leu Glu Asp Thr Val Arg Ala Lys Phe Pro Lys Ala Val Leu
                20                  25                  30
Gly Gln Gly Tyr Gly Met Thr Glu Ala Gly Pro Val Leu Thr Met Gly
                35                  40                  45
Leu Ala Phe Ala Lys Glu Pro Phe Pro Met Lys Pro Gly Ala Cys Gly
        50                  55                  60
Thr Val Val Arg Asn Ala Glu Ile Lys Ile Val Asp Thr Glu Asn Gly
65                  70                  75                  80
Gly Ser Leu Pro Arg Asn Thr Pro Gly Glu Ile Cys Ile Lys Gly Asp
                85                  90                  95
Gln Ile Met Lys Gly Tyr Leu Asn Asn Pro Glu Ala Thr Ala Ala Thr
                100                 105                 110
Ile Asp Asn Glu Gly Trp Leu His Thr Gly Asp Ile
        115                 120

<210> SEQ ID NO 89
<211> LENGTH: 333
<212> TYPE: PRT
<213> ORGANISM: Cucurbita maxima

<400> SEQUENCE: 89

Asp Leu Ser Ser Ile Arg Met Ile Lys Ser Gly Gly Ala Pro Leu Gly
1               5                   10                  15
Lys Glu Leu Glu Asp Thr Val Arg Ala Lys Phe Pro Lys Ala Val Leu
                20                  25                  30
Gly Gln Gly Tyr Gly Met Thr Glu Ala Gly Pro Val Leu Thr Met Gly
                35                  40                  45
Leu Ala Phe Ala Lys Glu Pro Phe Pro Met Lys Pro Gly Ala Cys Gly
        50                  55                  60
Thr Val Val Arg Asn Ala Glu Ile Lys Ile Val Asp Thr Glu Asn Gly
```

```
                65                  70                  75                  80
Gly Ser Leu Pro Arg Asn Thr Pro Gly Glu Ile Cys Ile Lys Gly Asp
                    85                  90                  95
Gln Ile Met Lys Gly Tyr Leu Asn Asn Pro Glu Ala Thr Ala Ala Thr
                100                 105                 110
Ile Asp Asn Glu Gly Trp Leu Ile Thr Leu Asp Gln Lys Thr Asn Gly
                115                 120                 125
Asp Glu Asn Gly Thr Tyr Leu Asn Phe Leu Pro Met Phe His Val Phe
            130                 135                 140
Gly Leu Val Cys Ile Thr Cys Ala Gln Leu Gln Arg Gly Asn Thr Ile
145                 150                 155                 160
Val Ser Met Pro Lys Phe Asn Leu Glu Lys Ala Leu Trp Ala Val Glu
                165                 170                 175
Lys Tyr Lys Val Thr Asp Leu Trp Val Val Pro Val Val Leu Ala
                180                 185                 190
Leu Ala Lys Gln Ser Val Val Lys Lys Tyr Asn Leu Ser Ser Leu Lys
                195                 200                 205
His Ile Gly Ser Gly Ala Ala Pro Leu Gly Lys Glu Leu Met Asp Glu
            210                 215                 220
Cys Ala Asn Asn Ile Pro Ser Ala Val Val Leu Gln Gly Tyr Gly Met
225                 230                 235                 240
Thr Glu Thr Cys Gly Val Val Ser Leu Glu Asn Arg Ala Val Gly Lys
                245                 250                 255
Arg Asn Thr Gly Ser Ala Gly Thr Leu Ala Ser Gly Val Glu Ala Gln
                260                 265                 270
Ile Val Ser Val Asp Thr Leu Lys Pro Leu Pro Pro Asn Gln Tyr Gly
                275                 280                 285
Glu Ile Leu Val Arg Gly Pro Asn Met Met Leu Gly Tyr Leu Asn Asn
            290                 295                 300
Pro Gln Ala Thr Lys Gln Thr Ile Asp Lys Tyr Gly Trp Val His Thr
305                 310                 315                 320
Gly Asp Leu Gly Tyr Phe Asp Glu Ala His Arg Arg Tyr
                    325                 330

<210> SEQ ID NO 90
<211> LENGTH: 208
<212> TYPE: PRT
<213> ORGANISM: Cucurbita maxima

<400> SEQUENCE: 90

Val Val Thr Arg Phe Arg Leu Ser Glu Gly Glu Gly Thr Phe Ile Cys
 1               5                  10                  15
Thr Val Pro Met Phe His Ile Tyr Gly Leu Val Ala Phe Ala Thr Gly
                20                  25                  30
Leu Leu Ser Ser Gly Ser Thr Ile Ile Val Leu Ser Lys Phe Glu Ile
                35                  40                  45
His Glu Met Leu Ser Ala Ile Glu Lys Tyr Arg Ala Thr Tyr Leu Pro
            50                  55                  60
Leu Val Pro Pro Ile Leu Val Ala Leu Val Asn Ala Ala Glu Gln Ile
65                  70                  75                  80
Lys Gly Lys Tyr Asp Leu Ser Ser Leu His Thr Ala Leu Ser Gly Gly
                85                  90                  95
Ala Pro Leu Gly Lys Glu Val Ile Glu Gly Phe Val Glu Lys Tyr Pro
                100                 105                 110
```

```
Asn Val Ala Ile Leu Gln Gly Tyr Gly Leu Thr Glu Ser Thr Gly Ile
        115                 120                 125

Gly Ala Ser Thr Asp Ser Leu Glu Glu Ser Arg Arg Tyr Gly Thr Ala
    130                 135                 140

Gly Leu Leu Ser Pro Ser Thr Glu Ala Met Ile Val Asp Pro Glu Thr
145                 150                 155                 160

Gly Glu Ala Leu Pro Val Asn Arg Thr Gly Glu Leu Trp Leu Arg Gly
                165                 170                 175

Pro Thr Val Met Lys Gly Tyr Phe Gly Asn Val Glu Ala Thr Ala Ser
            180                 185                 190

Thr Leu Asp Ser Met Gly Trp Leu Arg Thr Gly Asp Leu Cys Tyr Ile
        195                 200                 205
```

<210> SEQ ID NO 91
<211> LENGTH: 205
<212> TYPE: PRT
<213> ORGANISM: Cucumis sativa

<400> SEQUENCE: 91

```
Thr Lys Ser Leu Asn Pro Pro Tyr Pro Asn Pro Ser Ser Phe Phe Asn
1               5                   10                  15

Pro Ile Leu Ala Met Asp Ile Thr Met Asn Lys Ser Phe Asn Pro Gln
            20                  25                  30

Ser Gln Val Tyr Thr Ser Arg Arg Pro Ile His Phe Pro Thr Asp
        35                  40                  45

Pro Thr Ile Ser Ile Val Ser Phe Leu Phe Arg Asn Ser Ser Ser Tyr
    50                  55                  60

Pro Asn Ala Leu Ala Leu Val Asp Ala Asp Ser Gly Glu Ser Leu Thr
65                  70                  75                  80

Phe Arg Gln Leu Gln Ile Gln Val Ser Lys Leu Ala His Val Phe Ile
                85                  90                  95

Gln Leu Gly Ile Gln Lys Gly Asp Val Val Leu Ile Phe Ala Pro Asn
            100                 105                 110

Ser Ile His Phe Leu Val Cys Phe Phe Ala Ile Val Ala Ile Gly Ala
        115                 120                 125

Ile Ala Thr Thr Cys Asn Pro Ala Tyr Thr Ser Ala Glu Leu Ser Lys
    130                 135                 140

Gln Val Ala Asn Cys Lys Pro Lys Leu Val Ile Thr Val Pro Glu Leu
145                 150                 155                 160

Trp Asp Val Ile Gly Lys Leu Asn Leu Pro Ser Ile Ile Leu Gly Ser
                165                 170                 175

Lys Ile Ser Ser Lys Phe Ser Arg Ser Asn Ile Trp Ala Tyr Ser Asp
            180                 185                 190

Leu Ile Lys Lys Ala Gly Asp Val Ser Asn Leu Pro Val
        195                 200                 205
```

<210> SEQ ID NO 92
<211> LENGTH: 123
<212> TYPE: PRT
<213> ORGANISM: Cucurbita maxima

<400> SEQUENCE: 92

```
Ile Leu Tyr Ser Ser Gly Thr Thr Gly Arg Val Lys Gly Val Leu Leu
1               5                   10                  15

Ser His Arg Asn Leu Ile Ala Ser Ile Ser Ser Val Met Thr Leu Glu
            20                  25                  30
```

```
Ala Thr Ala Asp Glu Arg Glu Thr Glu Pro His Pro Val Ser Leu Tyr
        35                  40                  45

Leu Leu Pro Met Phe His Val Phe Gly Phe Tyr Met Met Ile Arg Ser
 50                      55                  60

Ile Ser Glu Gly His Thr Leu Val Leu Met Arg Lys Phe Gly Phe Glu
 65                  70                  75                  80

Glu Met Leu Arg Ala Val Glu Lys Tyr Arg Val Thr Tyr Ile Pro Val
                 85                  90                  95

Ser Pro Pro Leu Val Val Ala Met Val Lys Ser Glu Leu Val Ala Lys
                100                 105                 110

Tyr Asp Leu Ser Ser Leu Gln Ile Leu Gly Cys
        115                 120
```

<210> SEQ ID NO 93
<211> LENGTH: 171
<212> TYPE: PRT
<213> ORGANISM: Cucumis sativa

<400> SEQUENCE: 93

```
Gln Val Val Gly Leu Gln Arg Arg Val Glu Thr Asp Leu Asp Asn
 1               5                  10                  15

Leu Thr Phe Leu Lys Cys Cys Leu Lys Glu Thr Ile Arg Leu His Pro
                 20                  25                  30

Pro Ile Pro Leu Leu His Glu Ala Ala Glu Asp Ala Val Ile Ala
        35                  40                  45

Gly Tyr Phe Ile Pro Ala Lys Ser Arg Ile Met Val Asn Ala Trp Ala
 50                      55                  60

Ile Gly Arg Asp Pro Ala Ser Trp Asp Asp Ala Glu Thr Phe Arg Pro
 65                  70                  75                  80

Ala Arg Phe Leu Glu Glu Gly Val Pro Asp Phe Lys Gly Asn Asn Phe
                 85                  90                  95

Glu Phe Ile Pro Phe Gly Ser Gly Arg Arg Ser Cys Pro Gly Met Gln
                100                 105                 110

Leu Gly Leu Tyr Gly Leu Glu Ile Ala Val Ala His Leu Leu His Cys
                115                 120                 125

Phe Asp Trp Glu Leu Pro Asp Gly Met Lys Pro Ser Glu Met Asp Met
130                 135                 140

Ser Asp Val Phe Gly Leu Thr Ala Pro Arg Ala Thr Arg Leu Val Ala
145                 150                 155                 160

Val Pro Thr Lys Arg Val Leu Cys Pro Leu Leu
                165                 170
```

<210> SEQ ID NO 94
<211> LENGTH: 208
<212> TYPE: PRT
<213> ORGANISM: Cucurbita maxima

<400> SEQUENCE: 94

```
Met Ala Ser Thr Asn Asn Thr Pro Glu Asn Gln Asn Gln Ala Gly Arg
 1               5                  10                  15

His Gln Glu Val Gly His Lys Ser Leu Leu Gln Ser Asp Ala Leu Tyr
                 20                  25                  30

Gln Tyr Ile Leu Glu Thr Ser Val Tyr Pro Arg Glu Pro Glu Ser Met
        35                  40                  45

Lys Glu Leu Arg Glu Leu Thr Ala Lys His Pro Trp Asn Ile Met Thr
 50                      55                  60
```

```
Thr Ser Ala Asp Glu Gly Gln Phe Leu Asn Met Leu Lys Leu Ile
 65                  70                  75                  80

Asn Ala Lys Lys Thr Met Glu Ile Gly Val Tyr Thr Gly Tyr Ser Leu
                 85                  90                  95

Leu Ala Thr Ala Leu Ala Leu Pro Glu Asp Gly Gln Ile Leu Ala Met
            100                 105                 110

Asp Ile Asn Arg Glu Asn Tyr Glu Leu Gly Leu Pro Val Ile Glu Lys
            115                 120                 125

Ala Gly Val Ala His Lys Ile Glu Phe Lys Glu Gly Pro Ala Leu Pro
        130                 135                 140

Val Leu Asp Glu Met Val Ala Asp Glu Lys Asn His Gly Ser Tyr Asp
145                 150                 155                 160

Phe Ile Phe Val Asp Ala Asp Lys Asp Asn Tyr Ile Asn Tyr His Lys
                165                 170                 175

Arg Leu Ile Asp Leu Val Lys Val Gly Gly Leu Ile Gly Tyr Asp Asn
            180                 185                 190

Thr Leu Trp Asn Gly Ser Val Val Ala Pro Pro Asp Ala Pro Leu Arg
            195                 200                 205
```

<210> SEQ ID NO 95
<211> LENGTH: 141
<212> TYPE: PRT
<213> ORGANISM: Cucurbita maxima

<400> SEQUENCE: 95

```
Ile Leu Ala Met Asp Ile Asn Arg Glu Asn Tyr Glu Leu Gly Leu Pro
  1               5                  10                  15

Val Ile Glu Lys Ala Gly Val Ala His Lys Ile Glu Phe Lys Glu Gly
                 20                  25                  30

Pro Ala Leu Pro Val Leu Asp Glu Met Val Ala Asp Glu Lys Asn His
            35                  40                  45

Gly Ser Tyr Asp Phe Ile Phe Val Asp Ala Asp Lys Asp Asn Tyr Ile
        50                  55                  60

Asn Tyr His Lys Arg Leu Ile Asp Leu Val Lys Val Gly Gly Leu Ile
 65                  70                  75                  80

Gly Tyr Asp Asn Thr Leu Trp Asn Gly Ser Val Val Ala Pro Pro Asp
                 85                  90                  95

Ala Pro Leu Arg Lys Tyr Val Arg Tyr Tyr Arg Asp Phe Val Leu Glu
            100                 105                 110

Leu Asn Lys Ala Leu Ala Ala Asp Pro Arg Ile Glu Ile Cys Met Leu
            115                 120                 125

Pro Val Gly Asp Gly Ile Thr Leu Cys Arg Arg Ile Asn
        130                 135                 140
```

<210> SEQ ID NO 96
<211> LENGTH: 103
<212> TYPE: PRT
<213> ORGANISM: Cucumis sativa

<400> SEQUENCE: 96

```
Leu Ser Arg Leu His Ser Lys His Pro Ile Gln Pro Pro Ser Phe Gln
  1               5                  10                  15

Phe Asn Gln Ile Met Ala Asn Tyr His Ser Asp Lys Asn Ile Leu Lys
                 20                  25                  30

Ser Thr Ala Leu Leu Gln Tyr Ile Leu Lys Ala Asn Ala Tyr Pro Arg
            35                  40                  45
```

-continued

| | | | | | | | | | | | | | | |
|---|---|---|---|---|---|---|---|---|---|---|---|---|---|---|
| Glu | His | Glu | Gln | Leu | Lys | Glu | Leu | Arg | Glu | Ser | Thr | Phe | Asn | Lys | Phe |
| | 50 | | | | 55 | | | | | 60 | | | | | |
| Asp | Lys | Ser | Gly | Ser | Val | Met | Asn | Val | Pro | Val | Asp | Glu | Gly | Leu | Phe |
| 65 | | | | | 70 | | | | 75 | | | | | 80 | |
| Leu | Ser | Met | Leu | Leu | Lys | Leu | Met | Asn | Ala | Lys | Lys | Thr | Ile | Glu | Val |
| | | | | 85 | | | | | 90 | | | | 95 | | |
| Gly | Val | Tyr | Thr | Gly | Tyr | Ser | | | | | | | | | |
| | | | 100 | | | | | | | | | | | | |

METHODS FOR MODIFYING PLANT CELL WALLS AND MODIFIED PLANTS PRODUCED THEREBY

CROSS-REFERENCE TO RELATED APPLICATIONS

This application claims the benefit of U.S. Provisional Application No. 60/306,267, filed on Jul. 17, 2001, U.S. Provisional Application No. 60/306,327, filed on Jul. 17, 2001 and U.S. Provisional Application No. 60/345,397, filed on Nov. 9, 2001, which applications are incorporated herein by reference in their entirety.

FIELD OF THE INVENTION

This application relates to modification of cell walls in plants and, in particular, to the modification of secondary cell walls, including the modification of microfibril angles in S1 and/or S2 secondary cell wall layers, the modification of the relative thickness of the S1, S2 and/or S3 secondary cell wall layers, the modification of the degree of lignification of the S1, S2 and/or S3 secondary cell wall layers, the modification of the composition and/or relative amounts of lignin, lignin synthesis enzymes and intermediates, cellulose synthesis enzymes, including cellulose synthase and/or hemicellulose in the S1, S2 and/or S3 secondary cell walls, and plants having such modified cell walls. Trees, forage crops and other plants may be modified in accordance with the present invention.

BACKGROUND

Plant cells have rigid cell walls that determine the size, form and stability of the plant cell. These cell walls are comprised primarily of polymers of simple sugar monomers linked in a variety of linear or branched polymers known as polysaccharides. The most abundant simple sugar monomer is glucose, and the most abundant polymer is cellulose. Cellulose is a linear, unbranched polymer, comprised of β-1,4 linked glucose monomers. Other polysaccharides found in plant cell walls include hemicelluloses, which comprise a group of polysaccharides composed of β-1,4 linked glucose monomers having side chains which may include sugars other than glucose, including xylose, fucose, arabinose, and galactose. Hemicelluloses are a heterogeneous mixture of polysaccharides, the composition of which varies substantially for different plants. Hemicelluloses are defined, operationally, as that polymer fraction which may be extracted from the cell wall with alkali.

Pectins are another type of polysaccharide found in plant cell walls. Pectins are acidic polysaccharides, which are generally comprised primarily of galacturonic acid and rhamnose sugar monomers. Amylose, another common plant polysaccharide, is not a major component of cell walls, but instead acts primarily as a storage material for glucose, rather than as a structural polymer. Because amylose is composed primarily of α-1,4-linked glucose monomers, it is considered to be a related polymer from a biochemical and physiological perspective. The molecular structure of the cell wall and its biogenesis during growth are not completely understood.

The alignment of cellulose microfibrils in the cell wall changes during development of the plant cell. In isodiametric meristematic cells, the fibrils are oriented randomly in the plane of the wall. During the transition to extension growth, an increasingly parallel orientation of the newly deposited fibrils is observed. Cells that grow predominantly in one direction generally have parallel fibrils oriented generally perpendicular to the direction of growth. Plant cells having thick cell walls, such as epidermal and xylem cells, often have a multilayered microfibril structure. These walls may have thin layers of parallel fibrils, the direction of which changes from layer to layer by a substantially constant angle.

An important difference between the cell walls of trees and herbaceous plants is that tree cell walls have more complex xylem layers. The xylem types in cell walls of trees vary depending on the age of the tree and the position of the xylem in the tree. For example, young trees (less that eight years old for pine) or upper parts of the tree (with fewer than 6-8 growth rings) produce so-called juvenile wood xylem. Older parts of the tree produce so-called late wood xylem. Xylem cells have additional cellulose-rich secondary wall layers incorporated into the primary wall, which may become thickened and develop an increased tensile strength and resistance to pressure. The secondary cell wall comprises three additional layers, namely the S1, S2 and S3 layers. In mature wood and late wood (wood formed in autumn) the S2 layers are thicker and the cellulose fibrils have higher angles (both of which are commercially desirable traits), when compared to juvenile or early wood.

The secondary walls may comprise a considerable amount of lignin in addition to cellulose, pectins and hemicelluloses. The S1 layer is generally highly lignified, the S2 layer is lightly lignified, whereas the S3 layer is also highly lignified. Lignin is an insoluble polymer that is primarily responsible for the rigidity of plant stems. Specifically, lignin serves as a matrix around the polysaccharide components of some plant cell walls. In general, the higher the lignin content, the more rigid the plant. For example, tree species synthesize large quantities of lignin, with lignin constituting between 20% to 30% of the dry weight of wood. The lignin content of grasses ranges from 2-8% of dry weight and changes during the growing season. In addition to providing rigidity, lignin aids in water transport within plants by rendering cell walls hydrophobic and water impermeable. Lignin also plays a role in disease resistance of plants by impeding the penetration and propagation of pathogenic agents.

The presence and composition of lignin in plant cell walls is desirable for some applications and undesirable for others. In forestry trees, lignification reduces access by chemicals during pulping or during timber treatment. Similarly, in forage crops, the lignification reduces the digestibility of the forage crops for animals. Lignin is, however, an essential component of cell walls and provides structural support for the plant. Two major goals for the forestry industry are reduced rotation times and reduced costs of extracting pulp from wood. To reduce rotation times, young trees need to have enhanced growth characteristics, and have the wood characteristics of older trees. To reduce the costs of extracting pulp from wood, young trees need to have a reduced or modified lignin content. Similarly, for forage crops, an objective is to increase the digestibility and efficiency of the crop without adversely altering its growth and structural properties. By reducing lignin content of cereal stubble the time required to degrade the stubble in the soil will be greatly reduced. Furthermore by reducing the lignin content of high biomass producing cereals such as maize or sorghum the ability to utilize biomass for conversion to ethanol will be greatly enhanced.

Forage digestibility is affected by both lignin composition and concentration. Lignin is largely responsible for the digestibility, or lack thereof, of forage crops, with small increases in plant lignin content resulting in relatively high decreases (>10%) in digestibility (Buxton and Russell, *Crop Sci.* 28:538-558, 1988). For example, crops with reduced lignin content provide more efficient forage for cattle, with the yield of milk and meat being higher relative to the amount of forage crop consumed. During normal plant growth, an increase in the maturity of the plant stem is accompanied by a corresponding increase in lignin content and composition that causes a decrease in digestibility. This change in lignin composition is to one of increasing S:G ratio (syringyl/guaiacyl units). When deciding on the optimum time to harvest forage crops, farmers must therefore choose between a high yield of less digestible material and a lower yield of more digestible material.

As discussed in detail below, lignin is formed by polymerization of different monolignols that are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT Publication No. WO 94/23044. Furthermore, it has been shown that antisense expression of sequences encoding CAD in poplar leads to the production of lignin having a modified composition (Grand et al., *Planta* (Berl.) 163:232-237, 1985). Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens.

Lignin is formed by polymerization of at least three different monolignols, primarily para-coumaryl alcohol, coniferyl alcohol and sinapyl alcohol. While these three types of lignin subunits are well known, it is likely that slightly different variants of these subunits may be involved in the lignin biosynthetic pathway in various plants. For example, studies suggest that both free monolignols and monolignol-p-coumarate esters may be substrates for lignin formation in grasses. The relative concentration of the monolignol residues in lignin varies among different plant species and within species. The composition of lignin may also vary among different tissues within a specific plant. The three monolignols are derived from phenylalanine or tyrosine in a multistep process and are believed to be polymerized into lignin by a free radical mechanism.

Coniferyl alcohol, para-coumaryl alcohol and sinapyl alcohol are synthesized by similar pathways. The first step in the lignin biosynthetic pathway is the deamination of phenylalanine or tyrosine by phenylalanine ammonia-lyase (PAL) or tyrosine ammonia-lyase (TAL), respectively. In maize, the PAL enzyme also has TAL activity (Rosier et al., *Plant Physiol.* 113: 175-179, 1997). The product of TAL activity on tyrosine is p-coumarate. The product of PAL activity on phenylalanine is trans-cinnamic acid which is then hydroxylated by cinnamate 4-hydroxylase (C4H) to form p-coumarate. p-Coumarate is believed to be hydroxylated by coumarate 3-hydroxylase (C3H) to give caffeate. The newly added hydroxyl group is then methylated by caffeic acid O-methyl transferase (COMT) to give ferulate. More recently, a caffeoyl-CoA O-methyl transferase (CAMT) enzyme has been hypothesized to play a role in the lignin biosynthetic pathway (Ye et al., *Plant Physiol.* 108: 459-467, 1995).

Ferulate is conjugated to coenzyme A by 4-coumarate: CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (PER). The formation of sinapyl alcohol involves an additional enzyme, ferulate-5-hydroxylase (F5H). For a more detailed review of the lignin biosynthetic pathway, see Whetton R and Sederoff R, *The Plant Cell*, 7:1001-1013, 1995 and Whetten R et al., *Annu. Rev. Plant Physiol. Plant Mol. Biol.* 49:585-609, 1998.

Cellulose Synthesis

The major source of dietary fiber for grazing animals comes from plant cell walls. Mammals possess no enzymes capable for breaking down the polysaccharides in plant cell walls. Instead animals such as ruminants depend on microbial breakdown of plant cell walls through fermentation in either the rumen or large intestine.

Fiber in plants is measured using the Neutral Detergent Fiber (NDF) technique in which plant samples are boiled in a solution containing sodium lauryl sulfate (van Soest in "Nutritional Ecology of the Ruminant". Cornell University Press, Ithaca, N.Y., 1994). This detergent extracts water-soluble components such as sugars, lipids and organic acids. The remaining insoluble residue (fiber) is termed NDF and consists predominantly of plant cell wall components such as cellulose, hemicellulose, and lignin. The amount of cellulose and lignin in cell walls can be determined using the Acid Detergent Fiber (ADF) method where plant samples are boiled in sulfuric acid and sodium lauryl sulfate. The difference between NDF and ADF for a plant sample is normally considered to be the amount of hemicellulose (van Soest in "Nutritional Ecology of the Ruminant". Cornell University Press, Ithaca, N.Y., 1994).

Stems of most forage species have greater NDF content than leaves. For example, for a temperate $C_3$ grass in mid-flowering such as tall fescue (*Festuca arundinacea*), NDF content of leaves and stems is 50 and 70%, respectively (Buxton and Redfearn, *J. Nutrition* 127:S814-S818, 1997). In contrast, for a $C_4$ tropical grass such as switchgrass (*Panicum virgatum* L.) the NDF content of leaves and stems is 70 and 85%, respectively. The digestibility of a forage is determined by cell wall content, so that legumes are more digestible than grasses because they contain less NDF. The NDF of a legume, however, is generally less digestible than that of grasses because a higher proportion of the NDF is made up by lignin. The increase of lignin as a component of NDF is also responsible for the decrease in digestibility of grasses at the time of flowering. In fact, ruminants can digest only 40-50% of NDF in legumes compared to 60-70% for grass NDF (Buxton and Redfearn, *J. Nutrition* 127:S814-S818, 1997). Digestibility of cellulose by ruminants is therefore directly related to the extent of lignification. Generally hemicellulose is more digestible than cellulose.

Cellulose is the most abundant carbohydrate in forage making up to 20-40% of dry matter (van Soest in "Nutritional Ecology of the Ruminant". Cornell University Press, Ithaca, N.Y., 1994). The cellulose in forages consists predominantly of β1-4 glucan (85%) and smaller amounts of pentosans (e.g. xylose and arabinose; 15%). There appear to be two pools of cellulose within the plant cell wall, the difference being one is lignified and the other is not (van Soest in "Nutritional Ecology of the Ruminant". Cornell University Press, Ithaca, N.Y., 1994). The lignified cellulose is mostly found in the primary cell wall and in the S1 outer layer of the secondary cell wall. Independent of lignification, it appears that cellulose possesses variability in nutritive quality (van Soest in "Nutritional Ecology of the Ruminant". Cornell University Press, Ithaca, N.Y., 1994). This indicates that it is possible to alter the rate of cellulose digestibility by modifying the chemical composition of cellulose. This could be achieved through manipulating the actions of the cellulose synthesis and cellulose synthesis-like enzymes found in plant cells. One method to increase digestibility in this way is to increase the activity of the cellulose synthesis and cellulose synthesis-like enzymes responsible for synthesizing hemicellulose or to down regulate the cellulose synthesis and cellulose synthesis-like enzymes making cellulose. Hemicellulose is much more digestible than cellulose and is less likely to become lignified. Another way of manipulating cell wall composition is through modifying the rate and supply of primary components required for cellulose synthesis, i.e. of β1-4 glucan and pentosans such as xylose and arabinose. One way to achieve this is to modify the actions of soluble sucrose synthase and UDP glucose pyrophosphorylase enzymes that produce the UDP-glucose required for cellulose synthesis. This may be further modified by manipulating the actions of the large and small subunits of ADP-glucose pyrophosphorylase, the two enzymes that are rate-limiting steps in starch synthesis (Smith et al., *Ann. Rev. Plant Phys. Plant Mol. Biol.* 48:67-87, 1997).

Cellulose synthases are found in all tissues and cell types of plants and are involved in both primary and secondary cell wall biosynthesis. Cellulose synthase (cel or cesA) is a glycosyltransferase that utilizes UDP-glucose as a substrate in the polymerization of glucose residues to form 1,4-β-D-glucans (Richmond, *Genome Biology* I: reviews 3001.1-3001.6, 2000), thereby catalyzing the synthesis of cellulose (an aggregate of β-1,4-linked glucose residues as unbranched polymers). The CesA protein contains putative transmembrane domains and is thought to span the plasma membrane, where this catalytic component may interact with other proteins to form a cellulose synthase 'complex'. In plants, cesA proteins are encoded by a multi-gene family, of which ten have been identified from *Arabidopsis thaliana*, nine from maize (*Zea Mays*) and eight from rice (*Oryza sativa*) (Arioli et al., *Science* 279:717-720, 1998; Holland et al., *Plant Physiol.* 123:1313-1324, 2000). Differential expression of the *Arabidopsis* CesA genes suggests these genes have different functions within the plant.

In addition to the cellulose synthase genes described above, plants have a superfamily of cellulose synthase-like (CSL) genes, whose amino acid sequences are related to the CesA genes (Richmond and Somerville, *Plant Physiol.* 124:495-498, 2000; Richmond and Somerville, *Plant Mol. Biol.* 47: 131-143, 2001; Hazen et al., *Plant Physiol.* 128: 336-340, 2002). The CSL proteins are predicted to be integral membrane proteins and contain a highly conserved motif that is characteristics of glycosyl transferases. This family of proteins synthesizes repeating β-glycosyl subunits and the CSLs may be involved in the biosynthesis of plant cell wall components, for example hemicellulose. Using sequence data, the CSL superfamily can be divided into several distinct families, for example *Arabidopsis* has six CSL families (with 40+ members), whereas maize lacks one of these families but has a further two families.

Manipulating expression of genes in the cel/CSL superfamily would alter the chemical composition of plant cell walls in forage plants. Altering cell wall biosynthesis therefore provides an opportunity to increase digestibility of the plant dry matter. This may be achieved by increasing the amount of carbon in the plant allocated to cellulose biosynthesis at the expense of lignin biosynthesis. Alternatively, decreasing the amount of cellulose biosynthesis and increasing the amount of water-soluble carbohydrates would have a similar effect. Furthermore, specifically increasing hemicellulose levels in the plant cell walls at expense of cellulose would also increase forage digestibility. By utilizing specific promoters in combination with the cel and CSL genes it is possible to increase or decrease cellulose and hemicellulose levels in the leaf or stem.

SUMMARY OF THE INVENTION

The present invention provides methods for modulating cellulose, hemicellulose and lignin composition and deposition in secondary cell wall layers of plants to improve plant traits that are commercially desirable (e.g., enhanced digestibility of forage crops by animals, increased post-harvest processing of wood and crops for energy production and pulping, increase mechanical strength of plants, and others). In particular, the invention provides methods for use in (i) modulating microfibril angles in the S1, S2 and/or S3 layers of secondary cell walls; (ii) modifying the composition and deposition of lignin and/or cellulose and/or hemicellulose in S1, S2 and/or S3 secondary cell wall layers; (iii) modifying the thickness of S1, S2 and/or S3 secondary cell wall layers; (iv) identifying genes encoding transcription factors that regulate the modifications described above and the process of development of secondary cell walls; and (v) screening for inducers, repressors and modulators that effect the modifications described above. Preferably, these methods will use transcription factors that can be upregulated or downregulated in a tissue- and time-specific manner to restrict lignification in angiosperms to cell types that require lignin for structural support (e.g., vessel elements, extraxylary fibers), to eliminate or reduce lignification (and increase cellulose deposition) of tissues such as xylary fibers, fiber tracheids and tracheids and to increase the volume of the S2 layer in xylary fibers, fiber tracheids and tracheids (e.g., by repressing activation of the S3 layer or by preventing termination of cellulose deposition in the S2 layer). Likewise, in conifers, transcription factors will preferably be used to restrict lignification to latewood tracheids without affecting lignification in early wood, and more preferably, to restrict lignification in mid season wood, but not in early or late wood zones. Similarly, in forage crops and grasses, transcription factors will be preferably used to reduce the extent and type of lignification of stems to increase the digestibility for animals, reduce the time required for cereal stubble to degrade in the soil, and to improve the efficiency by which plant biomass is converted into ethanol.

The invention also encompasses modified plants that display modified microfibril angles in the S1, S2 and/or S3 secondary cell wall layers compared with unmodified native plants; modified plants that display modified composition and deposition of lignin and/or cellulose and/or hemicellulose in the S1, S2 and/or S3 secondary cell wall layers compared with unmodified native plants; modified plants that have modified thickness of S1, S2 and/or S3 secondary cell wall layers compared with unmodified native plants; and modified plants that have modified regulatory elements for modulating any of the above properties.

The invention also provides polynucleotide sequences, preferably from Cucurbitaceae (e.g., pumpkin and cucumber), but also from *Arabidopsis*, rice and from pine and Eucalyptus that encode enzymes that are involved in the synthesis of cellulose, hemicellulose, and lignin, transcription factors that regulate enzymes in the lignin biosynthetic pathway, and sequences encoding other cell wall polysaccharides, biosynthetic enzymes and cell wall proteins. The promoters of these sequences are isolated and used in DNA constructs for expressing transcription factors in desired cell types in plants or wood zones in trees. The polynucleotide sequences identified herein encode cellulose synthase (SEQ ID NOs 1-20), LIM Transcription Factors (SEQ ID NOs 21-25) caffeic acid 3-O-methyltransferase (cOMT) (SEQ ID NOs 26-33), 4-Coumarate: CoA ligase (4CL) (SEQ ID NOs 34-44), F5H (SEQ ID NO: 45) and caffeoyl-CoA O-Methyltransferase (ccOMT) (SEQ ID NOs 46-48). The predicted polypeptide sequences encoded by SEQ ID NOs 1-48 are listed in the Sequence Listing as SEQ ID NOs 49-96.

BRIEF DESCRIPTION OF FIGURES

FIG. 1. Amino acid sequence of SEQ ID NO: 1 showing conserved Cys residues of the N-terminal CxxC motif (boxed) and other conserved residues (boxed and in bold).

DETAILED DESCRIPTION

The present invention provides methods for modulating the composition and properties of secondary cell walls during plant growth and development. The methods comprise: identifying transcription factors in a plant species of interest that are candidates for use in modulating the expression of genes involved in the formation of secondary cell walls ("candidate transcription factors"); identifying genes involved in the formation of key components of secondary cell walls; and isolating the promoters of these genes for use in DNA constructs to increase or reduce the expression of candidate transcription factors in desired cell types in plants or wood zones in trees, thereby controlling the composition and deposition of lignin and/or cellulose and/or hemicellulose in S1, S2 and/or S3 secondary cell wall layers.

Polynucleotide sequences that encode: transcriptional activators or repressors of secondary cell wall biogenesis; enzymes involved in the synthesis, modification and/or turnover of cell wall components; and cortical microtubules (and associated proteins) of differentiating xylem cells are identified in a plant species of interest (e.g., model plant systems such as Arabidopsis, cucumber, pumpkin; forage crops and forestry trees). Expression constructs comprising sense and antisense orientations of selected polynucleotide sequences are introduced into plants for modulating the formation and composition of secondary cell walls. The resulting transgenic plants are analyzed for differences in secondary cell wall morphology and composition and plants with appropriate traits are selected for further modification and propagation. The biogenesis of secondary cell walls is a multistep, multigene process. Consequently, it is expected that improved cell wall qualities may require the expression or upregulation of combinations of genes that are not normally expressed in a particular plant species, or are expressed in that species, but not in combination. In addition, the repression or downregulation of particular genes or combinations of genes may also be required. A preferred approach, which has been mentioned above and is described in further detail below, is to identify transcription factors and use these to modulate key processes involved in secondary cell wall formation. Other useful approaches for modulation of multiple genes include crossing plants comprising different transgenes, concurrently introducing and expressing multiple genes into a plant (see, e.g., WO127241A2), and using gene silencing vectors comprising multiple sequences to reduce the expression of one or multiple genes (see, e.g., WO 99/49029, WO 99/53050, and WO 98/36083).

Identification of Candidate Genes

1. Candidate Transcription Factors

Transcription factors are initially selected from Arabidopsis databases. The transcription factors of interest may be rare and tightly regulated and or common and constitutively regulated.

The tightly regulated transcription factors are identified as "candidate transcription factors" in a functional assay for identifying heterologous plant genes, including transcription factors, that are involved in xylogenesis. The assay uses the Zinnia elegans mesophyll cell culture system and is described in U.S. Provisional Application 60/345,397. Briefly, the assay comprises culturing Zinnia mesophyll cells in tracheary element (TE)-inducing and non-inducing medium, transforming control cells with sham constructs (i.e., constructs that do not contain expressable heterologous polynucleotide sequences) and test cells with DNA constructs comprising promoters that are active during xylogenesis operably linked to coding regions of heterologous polynucleotide sequences to be tested, or reporter genes, and comparing xylogenesis in the test and control cells. Genes that encode transcriptional activators and repressors are assessed by cotransforming cells with sham- or test-genes and reporter genes and assessing the effect of test gene expression on the reporter gene signal. Genes that affect the morphology, architecture and composition of secondary cell walls can be identified based on analysis of tracheary element morphology, architecture, composition of secondary cell walls using microscopic techniques, flow cytometry, GC-MS, FTIR and other standard well-known chemical/biochemical/immunochemical methods. For the present purposes, promoter-reporter gene constructs can be used to determine whether promoters of candidate transcription factors are activated under TE-inducing conditions.

In addition, candidate transcription factors are identified directly by overexpressing the transcription factors in transgenic plants under a constitutive promoter such as the Super Ubiquitin promoter (see U.S. Pat. No. 6,380,459 and Example 6 below), or a xylem- or vascular tissue-specific promoter from Arabidopsis, rice and cucurbits (e.g., pumpkin, cucumber), for example. Cucurbit promoters have the advantage that they are not highly responsive to bending and can be used to identify transcription factors that activate processes involved in normal secondary cell wall formation, rather than secondary cell wall processes that are also influenced by bending stress.

2. Secondary Cell Wall Related Genes

Transgenic plants showing altered phenotypes are analyzed further to determine the genes that are regulated by the transcription factors. This analysis includes the use of microarrays comprising sequences of secondary cell wall related genes for transcriptional profiling and analysis of plant tissues for expression of reporter genes driven by promoters of secondary cell wall related genes using histochemical stains, transmission electron microscopy, confocal microscopy.

Microarray transcriptional profiling is performed on individual plants to identify which combinations of cell wall gene products are present during xylogenesis. The technique is well known to those of ordinary skill in the art and is also described briefly in Example 2. Transcription from various tissues of a plant or from plants that exhibit secondary cell wall defects may be analyzed to facilitate the identification of changes in expression of genes that are likely to be related to secondary, rather than primary, cell wall development. Microarray data analysis software is used for cluster analysis to identify transcripts that are specific to xylem development. Results of microarray transcriptional profiling are confirmed using real time RT-PCR.

In the present invention, the particular genes of interest for use in modulating plant quality include: genes involved in cellulose production, particularly those that are responsible for increasing the cellulose content of the S2 layer in the secondary cell wall; genes that control the amount and type of lignin, microtubule genes and genes for microtubule associated proteins which are expected to influence the orientation of cortical microtubules in differentiating secondary xylem cells, and transcription factors that are preferentially expressed during xylogenesis and may function as activators, repressors or coactivators of single or multiple genes involved in cellulose synthesis, hemicellulose synthesis, monolignol synthesis, lignification processes and other processes that determine plant quality. Full-length sequences of selected genes are obtained, and the genes are cloned into viral/binary vectors for in vitro and in planta expression and function testing, using art-recognized methods several of which are described in the Examples below.

EST libraries and databases for forestry and non-forestry plant species have been established from tissues that undergo secondary cell wall formation, as illustrated below in Example 1. Comparisons of the EST sequences in these libraries with sequences in other plant databases, including *Arabidopsis*, pumpkin and cucumber have identified homologs of xylem-specific transcription factors, cell cycle genes, genes for cell wall polysaccharides, cellulose synthases and cellulose synthase-like genes, and genes involved in lignin formation, among others.

Sequences of secondary cell wall related genes for use in the inventive methods are disclosed in SEQ ID NOs: 1-48 of the Sequence Listing. Representative examples of genes of interest are shown below.

| Component | Representative Examples |
|---|---|
| CELLULOSE | Cellulose synthase |
|  | Hexose pyrophosphorylase |
|  | Sucrose synthase |
| HEMICELLULOSE | Beta glucosidase |
|  | Hexose pyrophosphorylase |
|  | Sucrose phosphate synthase |
|  | Xyloglucan Endotransglycosylase |
|  | Arabinan synthase |
|  | Xylan synthase |
| LIGNIN | 4-coumarate CoA ligase |
|  | Cinnamoyl-CoA reductase |
|  | Coniferin beta-glucosidase |
|  | Coniferyl alcohol dehydrogenase |
|  | Mannitol dehydrogenase |
|  | Coniferyl-alcohol Glucosyltransferase |
|  | Laccase |
|  | Ferrulate 5-monooxygenase |
|  | para-Coumarate 3-monooxygenase |
|  | Trans-cinnamate 4-monooxygenase |
|  | Caffeate O-methyltransferase |
|  | Caffeoyl-CoA O-methyltransferase |
|  | Peroxidase |
| PECTIN | Hexose pyrophosphorylase |
|  | Pectinesterase |
|  | Polygalacturonase |

-continued

| Component | Representative Examples |
|---|---|
| STARCH | Alpha amylase |
|  | Hexose pyrophosphorylase |
|  | Starch branching enzyme |
|  | Starch synthase |
|  | Phenylalanine ammonia-lyase |
| TERPENOIDS | Terpenoid Synthases |
|  | Oxidosqualene |
| CELL WALL PROTEINS | Dirigent |
|  | Expansin |
|  | Arabinogalactan |
|  | Extensin |
|  | Yieldin |

Analysis of Functions of Candidate Genes

Genes that are candidates for enzymes involved in cell wall synthesis and lignification are expressed in vitro, and assayed for enzymatic activity. Cellulose deposition assays are carried out on cell lines stably transformed with cellulose biosynthesis genes. High throughput gene function assays are routinely used in the applicants' laboratories and include protoplast transformation assays, cell growth assays, promoter-reporter gene assays, tracheary element assays, and assays for cellulose and lignin synthesis.

Candidate genes can also be overexpressed in a model plant system such as *Arabidopsis* or tobacco plants to screen for genes that are involved in the control of formation of S1, S2 and S3 layers (e.g., homeobox genes and other transcriptional regulators). Transcription factors isolated from the xylem of plants used for wood production or as forage crops can be assayed in a model plant system, such as *Arabidopsis* or tobacco plants, by transforming and expressing wild-type and mutated forms of the factors and examining the resultant phenotypes. Gene silencing constructs and/or antisense constructs can be used to produce loss of function phenotypes which can be compared with phenotypes of wild-type or unmodified plants. The functional characterization of candidate genes includes the use of reverse genetic techniques to generate transgenic plants with loss of function mutations (e.g., T-DNA insertional mutagenesis, RNAi, Tilling, VIGS, and homologous recombination) and gain of function mutations (e.g., activation tagging). A transcription factor can be made constitutively active, for example, by translational fusion of the transcription factor to a VP16 activation domain. Similarly, a transcription factor can be made conditionally active, for example, by translationally fusing the transcription factor to a heterologous glucocorticoid receptor. Such techniques have been employed in the analysis of transcription factors in *Arabidopsis* (see, e.g., Riechmann and Ratcliffe, *Curr. Opin. Plant Biol.* 3:423-434 (2000)).

The temporal and spatial expression of genes of interest is examined by cloning the promoters specific for these genes, creating promoter-reporter fusion gene constructs and transforming plants with these constructs. Methods for cloning promoters, making promoter-reporter gene constructs, and transforming plants with these constructs are well known in the art. Promoter prediction programs are also well known (for examples, see Mount, "Bioinformatics", Cold Spring Harbor Laboratory Press, 2001, Chapter 8). The expression of the reporter protein, which is preferably GFP or another fluorescent protein, is monitored using epifluorescence microscopy on tissue sections. Localization of RNA transcripts in sectioned tissues may be performed on paraffin-embedded sectioned tissues essentially as described by Eshed et al., *Cell* 99:199-209 (1999) and cited references, and in fresh cut sections according to the methods of Xoconostle-Cazares et al., *Science* 283:94-98 (1999), Ruiz-Medrano et al., *Development* 126:4405-4419 (1999) and Koltai and Bird, *Plant Physiol.* 123:1203-1212 (2000).

Modulation of Expression in Transgenic Plants

Various constructs can be used to modulate lignin and/or cellulose content in developing secondary cell walls of plants to produce plants with improved properties. For example, constructs that comprise sense orientations of one or more genes selected from cellulose synthase genes, UDPG binding domains and UDPGPase, antisense orientations of selected lignin genes 4CL, LIM, and/or sense orientations of lignin genes Cald5H/F5H, CCoAOMT/AE-OMT are useful for modifying the polysaccharide and lignin content of cell walls. The 4CL or Super Ubiquitin (with intron) promoters optionally including modified enhancer elements are useful for directing the expression of genes in these constructs. For producing stronger wood with an increased amount of crystalline cellulose in forestry plants, it is advantageous to express transcription factors isolated from tension wood and cellulose-producing genes from this wood type. As described previously, constructs that comprise genes for modulating matrix composition (i.e., hemicelluloses and specific cell wall proteins) and constructs for use in coregulating the expression of more than one gene are also within the scope of the present invention.

METHODS AND EXAMPLES

The following examples and methods are offered by way of illustration and are not intended to limit the scope of the claimed invention.

The isolation and functional expression of genes encoding lignin biosynthesis enzymes in *P. radiata* and *E. grandis* is described in pending U.S. patent application Ser. Nos. 09/169,789 and 09/615,192, each of which is incorporated herein by reference in its entirety.

Modification of lignin reactivity in gymnosperms by changing the syringyl/guaiacyl ratio is described in U.S. Pat. No. 6,252,135, which is incorporated herein by reference in its entirety.

Example 1

Library Construction

A. *Eucalyptus grandis*

*Eucalyptus grandis* cDNA expression libraries (from various tissues, including flowers, leaves, phloem, roots, seeds, shoot buds and xylem) were constructed and screened as follows.

mRNA was extracted from the plant tissue using the protocol of Chang et al., *Plant Mol. Biol. Rep.* 11:113-116, 1993, with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactoside (X-gal) and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequences for positive clones were obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

B. *Lolium perenne* and *Festuca arundinacea*

In like manner, *L. perenne* and *F. arundinacea* cDNA expression libraries were constructed and screened. The tissues were taken at different times of the year, specifically in winter and spring, and from different parts of the plants, including leaf blades, leaf base, pseudostems, roots and stems, and were snap-frozen for storage prior to isolation of RNA.

C. Cucurbits

In like manner, cDNA libraries were prepared from vascular tissues of pumpkin (e.g. (*Cucurbita maxima*), melon (*Cucumis melo*), and cucumber (e.g. (*Cucumis sativus*) and screened. The databases were screened using publicly available homology search programs to identify structural homologs to previously identified genes and polypeptides from public databases. For example, FIG. 1 of the present application shows the predicted amino acid sequence encoded by SEQ ID NO: 1 and identifies conserved sequence features characteristic of cellulose synthase (Richmond, *Genome Biology* 1: 3001.1-3001.6, 2000).

Example 2

Microarray Transcriptional Profiling cDNA clones are arrayed onto glass slides as multiple replicas, with each location corresponding to a unique cDNA clone (as many as 5500 clones can be arrayed on a single slide, or chip). Each chip is hybridized with a pair of cDNA probes that are fluorescence-labeled with $Cy_3$ and $Cy_5$, respectively. RNA is prepared from stems or wood tissues sampled at multiple times during the growth and development of the plant or tree. Typically, 1 µg of polyA$^+$ RNA is used to generate each cDNA probe. After hybridization, the chips are scanned and the fluorescence intensity recorded for both $Cy_3$ and $Cy_5$ channels. There are multiple built-in quality control steps. First, the probe quality is generally monitored using a panel of ubiquitously expressed genes. Secondly, the control plate also can include yeast DNA fragments of which complementary RNA may be spiked into the probe synthesis for measuring the quality of the probe and the sensitivity of the analysis. Currently, the technology offers a sensitivity of about 1 in 100,000 copies of mRNA. Finally, the reproducibility of this technology can be ensured by including duplicated control cDNA elements at different locations.

Example 3

Comparison of *P. radiata*, *E. grandis* and *Arabidopsis thalinana* cellulose Synthase and Cellulose Synthase-Like Genes Comparison of EST sequences from *P. radiata*, *E. grandis* and *Arabidopsis thaliana* databases revealed both similarities (+) and differences (−), as shown in the Table below.

| Ath group | Arabidopsis thaliana | Pinus radiata | E. grandis |
|---|---|---|---|
| AtCesA01(RSW1) | + | − | + |
| AtCesA02,05,06,09 | + | − | + |
| AtCesA03 | + | + | + |
| AtCesA07(IRX3) | + | + | + |
| AtCesA08(IRX1) | + | + | + |
| Cs1A | + | + | − |
| Cs1B | + | − | − |
| Cs1C | + | + | + |
| Cs1D | + | − | − |
| Cs1E | + | + | − |
| Cs1G | + | − | + |

Example 4

Use of an O-methyltransferase (OMT) Gene to Modify Lignin Biosynthesis a) Transformation of tobacco plants with a *Pinus radiata* OMT gene Sense and anti-sense constructs containing a polynucleotide including the coding region of OMT from *Pinus radiata* were inserted into *Agrobacterium tumefaciens* LBA4301 (provided as a gift by Dr. C. Kado, University of California, Davis, Calif.) by direct transformation using published methods (see, An G, Ebert P R, Mitra A, Ha SB: Binary Vectors. In: Gelvin S B, Schilperoort R A (eds) *Plant Molecular Biology Manual*, Kluwer Academic Publishers, Dordrecht (1988)). The presence and integrity of the transgenic constructs were verified by restriction digestion and DNA sequencing.

Tobacco (*Nicotiana tabacum* cv. Samsun) leaf sections were transformed using the method of Horsch et al., *Science* 227:1229-1231, 1985. Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 1 below indicates that the transformed plant lines were confirmed as independent transformed lines.

b) Expression of *Pinus* OMT in Transformed Plants

Total RNA was isolated from each independent transformed plant line created with the OMT sense and anti-sense constructs. The RNA samples were analyzed in Northern blot experiments to determine the level of expression of the transgene in each transformed line. The data shown in the column labeled "Northern" in Table 1 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridization to RNA samples from empty vector-transformed control plants.

c) Modulation of OMT Enzyme Activity in Transformed Plants

The total activity of OMT enzyme, encoded by the *Pinus* OMT gene and by the endogenous tobacco OMT gene, in transformed tobacco plants was analyzed for each transformed plant line created with the OMT sense and anti-sense constructs. Crude protein extracts were prepared from each transformed plant and assayed using the method of Zhang et al., *Plant Physiol.* 113:65-74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of *Pinus* OMT on Lignin Concentration in Transformed Plants

The concentration of lignin in the transformed tobacco plants was determined using the well-established procedure of thioglycolic acid extraction (see, Freudenberg et al., in *Constitution and Biosynthesis of Lignin*, Springer-Verlag, Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labeled "TGA" in Table 1 shows that the transformed plant lines containing the sense and the anti-sense OMT gene constructs all exhibited significantly decreased levels of lignin, relative to the empty vector-transformed control plant lines.

TABLE 1

| Plant line | Transgene | Orientation | Southern | Northern | Enzyme | TGA |
|---|---|---|---|---|---|---|
| 1 | control | na | + | blank | 100 | 104 |
| 1 | OMT | sense | + | 2.9E+6 | 86 | 55 |
| 2 | OMT | sense | + | na | 162 | 58 |
| 3 | OMT | sense | + | 4.1E+6 | na | 63 |
| 4 | OMT | sense | + | 2.3E+6 | 142 | 66 |
| 5 | OMT | sense | + | 3.6E+5 | 199 | 75 |
| 1 | OMT | anti-sense | + | 1.6E+4 | 189 | 66 |
| 2 | OMT | anti-sense | + | 5.7E+3 | 35 | 70 |
| 3 | OMT | anti-sense | + | 8.0E+3 | 105 | 73 |
| 4 | OMT | anti-sense | + | 1.4E+4 | 109 | 74 |
| 5 | OMT | anti-sense | + | 2.5E+4 | 87 | 78 |
| 6 | OMT | anti-sense | + | 2.5E+4 | 58 | 84 |
| 7 | OMT | anti-sense | + | 2.5E+4 | 97 | 92 |
| 8 | OMT | anti-sense | + | 1.1E+4 | 151 | 94 |

Example 5

Use of a 4-Coumarate:CoA Ligase (4CL) Gene to Modify Lignin Biosynthesis a) Transformation of Tobacco Plants with a *Pinus radiata* 4CL Gene Sense and anti-sense constructs containing a Polynucleotide including the coding region of 4CL from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blot experiments. A "+" in the column labeled "Southern" in Table 2 indicates that the transformed plant lines listed were confirmed as independent transformed lines.

b) Expression of *Pinus* 4CL in Transformed Plants

Total RNA was isolated from each independent transformed plant line created with the 4CL sense and anti-sense constructs. The RNA samples were analyzed in Northern blot experiments to determine the level of expression of the transgene in each transformed line. The data shown in the column labeled "Northern" in Table 2 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridization to RNA samples from empty vector-transformed control plants.

c) Modulation of 4CL Enzyme Activity in Transformed Plants

The total activity of 4CL enzyme, encoded by the *Pinus* 4CL gene and by the endogenous tobacco 4CL gene, in transformed tobacco plants was analyzed for each transformed plant line created with the 4CL sense and anti-sense constructs. Crude protein extracts were prepared from each transformed plant and assayed using the method of Zhang et al., *Plant Physiol.* 113:65-74, 1997). The data contained in the column labeled "Enzyme" in Table 2 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of *Pinus* 4CL on Lignin Concentration in Transformed Plants

The concentration of lignin in samples of transformed plant material was determined as described in Example 3. The data shown in the column labeled "TGA" in Table 2 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthetic gene such as 4CL.

TABLE 2

| plant line | transgene | orientation | Southern | Northern | Enzyme | TGA |
|---|---|---|---|---|---|---|
| 1 | control | na | + | blank | 100 | 92 |
| 2 | control | na | + | blank | 100 | 104 |
| 1 | 4CL | sense | + | 2.3E+4 | 169 | 64 |
| 2 | 4CL | sense | + | 4.5E+4 | 258 | 73 |
| 3 | 4CL | sense | + | 3.1E+4 | 174 | 77 |
| 4 | 4CL | sense | + | 1.7E+4 | 164 | 80 |
| 5 | 4CL | sense | + | 1.6E+4 | 184 | 92 |
| 1 | 4CL | anti-sense | + | na | 59 | 75 |
| 2 | 4CL | anti-sense | + | 1.0E+4 | 70 | 75 |
| 3 | 4CL | anti-sense | + | 9.6E+3 | 81 | 80 |
| 4 | 4CL | anti-sense | + | 1.2E+4 | 90 | 83 |
| 5 | 4CL | anti-sense | + | 4.7E+3 | 101 | 88 |
| 6 | 4CL | anti-sense | + | 3.9E+3 | 116 | 89 |
| 7 | 4CL | anti-sense | + | 1.8E+3 | 125 | 94 |
| 8 | 4CL | anti-sense | + | 1.7E+4 | 106 | 97 |

Example 6

Isolation, Cloning and Expression of Promoters for Use in Genetic Constructs of the Present Invention A. Isolation and Cloning of a Superubiquitin Promoter from *Pinus radiata*

*Pinus radiata* cDNA expression libraries were constructed and screened by the method described in Example 1.

Isolation of cDNA Clones Containing the Ubiquitin Gene:

Sequences of cDNA clones with homology to the ubiquitin gene were obtained from high-throughput cDNA sequencing as described above. Sequences from several independent clones were assembled in a contig and a consensus sequence was generated from overlapping clones.

Cloning of the Super Ubiquitin Promoter:

Fragments of the Super Ubiquitin promoter were cloned by two different PCR-based approaches.

Method 1: Long Distance Gene Walking PCR

Using "Long Distance Gene Walking" PCR (Min & Powell, *Biotechniques* 24:398-400, 1998), a 2 kb fragment was obtained that contained the entire coding region of the ubiquitin gene, a 900 bp intron in the 5' UTR and approximately 100 bp of the promoter.

To generate this fragment, 2 nested primers were designed from the 3' UTR of the Super Ubiquitin cDNA sequence isolated from pine. Generally, the 5' UTR is used for primer design to amplify upstream sequence. However, the available 5' UTR of Super Ubiquitin was very short, and two initial primers derived from this region failed to amplify any fragments. Therefore, specific primers were designed from the 3' UTR.

The final PCR product contained fragments of different sizes. These fragments were separated by electrophoresis and the largest were purified from the gel, digested with restriction endonuclease NotI and cloned in the NotI site of expression vector pBK-CMV (Stratagene, La Jolla, Calif.). The largest of these clones contained the complete coding region of the gene (no introns were found in the coding sequence) and a 5' UTR which contained a 900 bp intron.

Method 2: "Genome Walker" Kit

The Super Ubiquitin gene promoter was cloned using a "Genome Walker" kit (Clontech, Palo Alto, Calif.). This is also a PCR-based method, which requires 2 PCR primers to be constructed, one of which must be gene-specific. Although the ubiquitin coding region is highly conserved, the 5' UTR from different ubiquitin genes is not conserved and could therefore be used to design a gene-specific primer. A 2.2 kb fragment was amplified and subcloned in pGEM-T-easy (Promega, Madison, Wis.). Analysis by PCR and DNA sequencing showed that the clone contained 5' UTR sequence of the Super Ubiquitin gene, including the 900 bp intron and approximately 1 kb of putative promoter region. An intron in the 5' UTR is a common feature of plant polyubiquitin genes and may be involved in determining gene expression levels.

Expression of Super Ubiquitin:

Using primers derived from the gene-specific 5' and 3' UTR sequences, expression levels of Super Ubiquitin in different plant tissues was examined by means of RT-PCR. Super Ubiquitin was found to be expressed in all plant tissues examined, including branch phloem and xylem, feeder roots, fertilized cones, needles, one year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5'UTR.

Functional Analysis of the Super Ubiquitin Promoter:

To test the function of the Super Ubiquitin promoter in plants, *Arabidopsis thaliana* was transformed with constructs containing the reporter gene for Green Fluorescent Protein (GFP) operably linked to the Super Ubiquitin promoter either with or without the intron. Constructs lacking a promoter were used as a negative control, with a plant T-DNA vector carrying a CaMV 35S promoter cloned in front of GFP being used as a positive control. The constructs were introduced into *Arabidopsis* via *Agrobacterium*-mediated transformation.

All the plant culture media were according to the protocol of Valvekens and Van Montagu, *Proc. Natl. Acad. Sci. USA* 85:5536-5540, 1998 with minor modifications. For root transformation, sterilized seeds were placed in a line on the surface of germination medium, the plates were placed on their sides to facilitate root harvesting, and the seeds were grown for two weeks at 24° C. with 16 h photoperiod.

Expression of the constructs was measured by determining expression levels of the reporter gene for Green Fluorescent Protein (GFP). Preliminary GFP expression (transient) was detected in early transgenic roots during T-DNA transfer. Transgenic roots that developed green callus, growing on shoot-inducing medium containing 50 μg/ml Kanamycin and 100 μg/ml Timentin, were further tested for GFP expression. After several weeks of stringent selection on Kanamycin medium, several independent transgenic *Arabidopsis* lines were engineered and tested for GFP expression.

Expression was seen both with the Super Ubiquitin promoter including intron and the Super Ubiquitin promoter without the intron. However, preliminary results indicated that the levels of expression obtained with the Super Ubiquitin intron-less promoter construct were significantly higher than those seen with the promoter including intron, suggesting that the intron may contain a repressor.

Expression Levels of Promoter in Different Plant Tissues

Expression levels of Super Ubiquitin in different plant tissues was examined by means of RT-PCR. Super Ubiquitin was found to be expressed in all plant tissues examined, including branch phloem and xylem, feeder roots, fertilized cones, needles, one-year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5'UTR.

B. Isolation and Cloning of Promoters for Genes Involved in Secondary Cell Wall Formation In like manner, gene-specific promoters are isolated, cloned and tested.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

---

We claim:

1. A method for modulating gene expression involved in secondary cell wall formation comprising:
   (a) transforming a plant cell with a DNA construct comprising a promoter sequence operably linked to a polynucleotide encoding a candidate transcription factor;
   (b) regenerating the plant cell to provide a transgenic plant;
   (c) expressing the DNA construct in the cells of the transgenic plant and selecting a transgenic plant with an altered phenotype compared to the phenotype of a nontransformed plant; and
   (d) determining whether gene expression involved in secondary cell wall formation is modulated, wherein the candidate transcription factor is a LIM Transcription Factor having SEQ ID NO: 21.

2. The method of claim 1, wherein the candidate transcription factor is identified by determining that the promoter of the transcription factor is active during secondary cell wall formation.

3. The method of claim 1, wherein the candidate transcription factor is identified by expressing the transcription factor in a transgenic plant and detecting an altered phenotype that is associated with changes in secondary cell wall formation.

* * * * *